US008226933B2

(12) United States Patent
Granger et al.

(10) Patent No.: US 8,226,933 B2
(45) Date of Patent: Jul. 24, 2012

(54) METHOD FOR TREATING SKIN WITH BOOSTER COMPOSITIONS

(75) Inventors: Stewart Paton Granger, Bedford (GB); Ian Richard Scott, Edgewater, NJ (US); Robert Mark Donovan, Bedford (GB); Susanne Teklits Iobst, Maywood, NJ (US); Lisa Licameli, Dumont, NJ (US)

(73) Assignee: Unilever Home & Personal Care, USA division of Conopco, Inc., Greenwich, CT (US)

( * ) Notice: Subject to any disclaimer, the term of this patent is extended or adjusted under 35 U.S.C. 154(b) by 0 days.

(21) Appl. No.: 13/097,142

(22) Filed: Apr. 29, 2011

(65) Prior Publication Data
US 2011/0206626 A1  Aug. 25, 2011

Related U.S. Application Data

(60) Continuation of application No. 12/045,339, filed on Mar. 10, 2008, now Pat. No. 7,959,913, which is a division of application No. 10/312,659, filed as application No. PCT/EP01/07234 on Jun. 25, 2001, now abandoned.

(60) Provisional application No. 60/215,301, filed on Jun. 30, 2000.

(51) Int. Cl.
*A61K 8/00* (2006.01)
*A61Q 17/04* (2006.01)
*A61Q 19/00* (2006.01)
*A61Q 19/02* (2006.01)

(52) U.S. Cl. ........... 424/59; 424/62; 424/94.1; 514/529; 514/559; 514/703; 514/725

(58) Field of Classification Search .................... 424/59, 424/62, 94.1; 514/529, 559, 703, 725
See application file for complete search history.

(56) References Cited

U.S. PATENT DOCUMENTS

| | | |
|---|---|---|
| 5,028,628 A | 7/1991 | Tadepalli et al. |
| 5,037,829 A | 8/1991 | Freyne et al. |
| 5,151,421 A | 9/1992 | Venet et al. |
| 5,476,852 A | 12/1995 | Cauwenbergh |
| 5,500,435 A | 3/1996 | Van Wauwe et al. |
| 5,536,740 A | 7/1996 | Granger et al. |
| 5,583,136 A | 12/1996 | Yusuf et al. |
| 5,599,548 A | 2/1997 | Granger et al. |
| 5,612,354 A | 3/1997 | Sanz et al. |
| 5,665,367 A | 9/1997 | Burger et al. |
| 5,693,330 A | 12/1997 | Granger et al. |
| 5,716,627 A | 2/1998 | Granger et al. |
| 5,723,139 A | 3/1998 | Granger et al. |
| 5,747,049 A | 5/1998 | Tominaga |
| 5,747,051 A | 5/1998 | Granger et al. |
| 5,756,109 A | 5/1998 | Burger et al. |
| 5,759,556 A | 6/1998 | Burger et al. |
| 5,766,575 A | 6/1998 | Crotty et al. |
| 5,811,110 A | 9/1998 | Granger et al. |
| 5,817,646 A | 10/1998 | Gossioux |
| 5,849,310 A | 12/1998 | Trinh et al. |
| 5,853,705 A | 12/1998 | Nakayama et al. |
| 5,885,595 A | 3/1999 | Corey et al. |
| 5,955,092 A | 9/1999 | Granger et al. |
| 5,976,555 A | 11/1999 | Liu et al. |
| 6,019,990 A | 2/2000 | Remmereit |
| 6,949,247 B2 | 9/2005 | Granger et al. |
| 7,959,913 B2 | 6/2011 | Granger et al. |
| 2002/0142016 A1 | 10/2002 | Granger et al. |
| 2002/0143059 A1 | 10/2002 | Pillai et al. |
| 2004/0043044 A1 | 3/2004 | Granger et al. |

FOREIGN PATENT DOCUMENTS

| | | |
|---|---|---|
| EP | 0803247 | 10/1997 |
| EP | 0803248 A2 | 10/1997 |
| WO | WO9309805 | 5/1993 |
| WO | WO9319743 | 10/1993 |
| WO | WO9813020 | 4/1998 |
| WO | WO0108650 A1 | 2/2001 |

OTHER PUBLICATIONS

Anders Vahlquist, Dec. 12, 1989, Isotretinoin Treatment of Severe Acne Affects the Endogenous Concentration of Vitamin A in Sebaceous Glands, J Invest Dermatol 1990 vol. 94 pp. 496-498, vol. 94, 496-498.
Barua, 1990, Analysis of Water-Soluble Compounds: Glucuronides, Methods in Enzymology, 189, 136-145.
Charles N. Ellis, J J. Voorhees, 1989, Treatment of Actinically Aged Skin with Topical Tretinoin, Pharmacology of Retinoids in the Skin, vol. 3, pp. 249-252.
John C. Saari and D. Lucille Bredberg, 1988, CoA and Non-CoA-dependent Retinol Esterification, CoA-and Non-CoA-dependent Retinol Esterification in Retinal Pigment Epithelium, vol. 263 No. 17, pp. 8084-8090, the Journal of Biological Chemistry.
John C. Saari and D. Lucille Bredberg, 1990, Acyl-CoA:Retinol Acyltransferase and Lecithin:Retinol, Tissue and Organ Culture, vol. 190, pp. 156-163, Academic Press Inc.
Martini et al., May 15, 1993, Participation of P450 3A Enzymes in Rat Hepatic Microsomal Retinoic Acid 4-0Hydroxylation, Archives of Biochemistry and Biophysics, vol. 303 No. 1, 57-66.
Napoli et al., May 15, 1987, The Biosynthesis of Retinoic Acid from Retinol by Rat Tissues in Vitro, Arvhies of Biochemistryand Biophysics, 255, 95-101.
Nicholas J. Lowe, Michael David, 1989, Pharmacology of Retinoids in the Skin, Pharmacology and the Skin, vol. 3, pp. 240-248, B. Shrrot, H. Schefer.
International Search Report PCT/EP01/07234 dated Dec. 16, 2002.

*Primary Examiner* — Herbert J Lilling
(74) *Attorney, Agent, or Firm* — Edward A. Squillante, Jr.

(57) ABSTRACT

A skin care product comprising from about 0.001% to about 10% of a retinoid, in combination with 0.0001% to about 50% of a combination of retinoid boosters.

14 Claims, No Drawings

METHOD FOR TREATING SKIN WITH BOOSTER COMPOSITIONS

This is a continuation Application of U.S. Ser. No. 12/045,339, filed Mar. 10, 2008, now U.S. Pat. No. 7,959,913 which is a divisional of U.S. application Ser. No. 10/312,659 filed Aug. 11, 2003 now abandoned and which is a 371 of PCT/ER01/07234 filed Jun. 25, 2001 and which claims priority to provisional application 60/215,301 filed Jun. 30, 2000.

The present invention relates to cosmetic skin conditioning compositions containing certain compounds which mimic the effect on skin of retinoic acid.

Retinol (vitamin A) is an endogenous compound which occurs naturally in the human body, and is essential for normal epithelial cell differentiation. Natural and synthetic vitamin A derivatives have been used extensively in the treatment of a variety of skin disorders and have been used as skin repair or renewal agents. Retinoic acid has been employed to treat a variety of skin conditions, e.g., acne, wrinkles, psoriasis, age spots and discoloration. See e.g., Vahlquist, A. et al., *J. Invest. Dermatol.*, Vol. 94, Holland D. B. and Cunliffe, W. J. (1990), pp. 496-498; Ellis, C. N. et al., "Pharmacology of Retinols in Skin", Vasel, Karger, Vol. 3, (1989), pp. 249-252; Lowe, N. J. et al., "Pharmacology of Retinols in Skin", Vol. 3, (1989), pp. 240-248; PCT Patent Application No. WO 93/19743.

It is believed that retinol esters and retinol are enzymatically converted in the skin into retinoic acid according to the following mechanism:

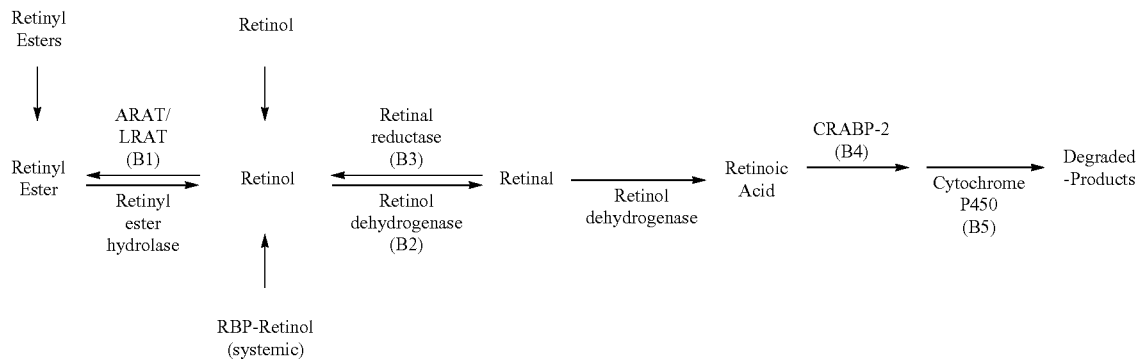

Retinol metabolism in the epidermis: enzyme names

The present invention is based on the discovery that certain compounds enhance the conversion of retinyl esters and retinol to retinoic acid. The compounds are collectively termed "boosters" and are coded as groups B1 to B5 according to the boosting mechanism of the particular compound. The mechanism of the booster groups is as follows: inhibiting ARAT/LRAT (AcylCoenzymeA (CoA): retinal acyl transferase/Lecithin: retinal acyl transferase) activity (B1), enhancing retinol dehydrogenase activity (B2), inhibiting retinal reductase activity (B3), antagonising CRABP-II (Cellular Retinoic Acid Binding Protein II) binding of retinoic acid (B4) and inhibiting cytochrome P450 dependent retinoic acid oxidation (B5).

The boosters alone or in combination with each other potentiate the action of retinoids by increasing the conversion of the retinoids to retinoic acid and preventing the degradation of retinoic acid. The boosters act in conjunction with a retinoid (e.g. retinol, retinyl esters, retinal, retinoic acid), the latter being present endogenously in the skin. The preferred compositions, however, include a retinoid in the composition, co-present with a booster or a combination of boosters, to optimise performance.

Several patents by Granger et al describe the use of retinoid boosters in cosmetic compositions to improve the efficacy of retinol and retinyl esters (U.S. Pat. Nos. 5,759,556, 5,756,109, 5,747,051, 5,716,627, 5,811,110, 5,536,740, 5,747,051, 5,599,548, 5,955,092, 5,885,595, 5,759,556, 5,693,330). The boosters described in these patents are restricted to class B1 and B5. Furthermore Johnson & Johnson have a series of patents which describe the use of molecules which fall into class 5 booster molecules (U.S. Pat. Nos. 5,028,628; 5,037,829; 5,151,421; 476,852; 5,500,435; 5,583,136; 5,612,354).

The molecules which act as retinoid boosters are common ingredients in cosmetic products. There is considerable prior art describing their use in cosmetic compositions. There is substantial prior art describing the use of two or more of these molecules in the same composition. Some of the examples of the prior art are as in U.S. Pat. Nos. 5,665,367, 5,747,049, 5,853,705, 5,766,575, and 5,849,310.

However, the prior art does not describe synergy arising from combinations of booster molecules. This observation of a synergistic boosting of retinoid activity from combinations of booster molecules was an unexpected finding. The prior art does not describe optimal concentrations or ratios of booster molecules or ratios of booster molecules to that of retinoids. Thus, the present invention is novel in that by combining cosmetic retinoids with booster molecules, at the most appropriate concentrations or ratios, a substantial improvement in efficacy of the retinoids is obtained.

The classes of boosters suitable for use in the present invention include but are not limited to the boosters listed in Tables B1 through to B5.

Best Groups of Boosters

B1 Compounds

| | |
|---|---|
| 1. Fatty Acid Amides | These are readily commercially available and have the added advantage of being surfactants and thus help generate emulsions suitable for cosmetic preparations. |
| 2. Ceramides | These can additionally act as precursors of stratum corneum barrier ceramides. |
| 3. Carotenoids | These can offer some UV protection and and act as natural colorants. |
| 4. Flavonoids | Natural antioxidants. |

-continued

| | |
|---|---|
| 5. Cyclic fragrances | These are readily commercially available and additionally can be used to fragrance the product. |
| 6. Non-cyclic fragrances | These can be used to fragrance the product. |
| 7. Phospholipid analogues | These can be utilised by skin cells to nourish the generation of barrier components. |
| 8. Ureas | These are readily commercially available and can also act as preservatives for the product. |

B2 Compounds

| | |
|---|---|
| 1. Phosphatidyl choline | Most preferred as most active activator of Retinol Dehydrogenase |
| 2. Sphingomyelin | |

B3 Compounds

| | |
|---|---|
| Arachidonic Acid Linoleic Acid Linolenic Acid Myristic Acid | Fatty Acids which can be useful in maintaining stratum corneum barrier |
| Linoleic Acid Linolenic Acid | Essential Fatty Acids |
| Arachidonic Acid Myristic Acid | Non-essential fatty acids |
| Glycyrrhetinic Acid | Polycyclic triterpene carboxylic acid which is readily obtained from plant sources. |
| Phosphatidyl ethanolamine | Can be incorporated into cellular membranes. |

B4 Compounds

| | |
|---|---|
| Hexadecanedioic acid 12-hydroxystearic acid Isostearic acid | Saturated fatty acids. |
| Linseed oil Elaidic acid | Unsaturated fatty acids |
| Elaidic acid Isostearic acid Hexadecanedioic acid | Solid at room temperature |
| Linseed oil 12-hydroxystearic acid | Liquid at room temperature |

B5 Compounds

| | |
|---|---|
| Bifonazole Climbazole Clotrimazole Econazole Ketoconazole Miconazole | Antimicotics |
| Climbazole | Readily commercially available |
| Lauryl hydroxyethylimidazoline | Compounds which are readily commercially available and have the added advantage of being surfactants and thus help generate emulsions suitable for cosmetic preparations. |
| Quercetin | Naturally occuring flavanoid which has antioxidant properties. |
| Coumarin | Natural colorant |
| Quinolines | |
| Isoquinolines | |
| Metyrapone | |

The present invention includes, in part, a skin conditioning composition containing from about 0.0001% to about 50%, preferably from 0.001% to 10%, most preferably from 0.001% to 5% by weight of the composition of a booster or combination of boosters and a cosmetically acceptable vehicle.

The boosters or combinations thereof included in the inventive compositions are selected from the group consisting of:
(a) a booster selected from the group consisting of B2; B3; B4;
(b) binary combinations of boosters selected from the group consisting of:
B1/B2; B1/B3; B1/B4; B1/B5; B2/B3, B2/B4; B2/B5, B3/B4; B3/B5; B4/B5
(c) ternary combinations of boosters selected from the group consisting of:
B1/B2/B3; B1/B2/B4; B1/B2/B5; B1/B3/B4; B1/B3/B5; B1/B4/B5; B2/B3/B4; B2/B3/B5; B2/B4/B5; B3/B4/B5
(d) quaternary combinations of boosters selected from the group consisting of:
B1/B2/B3/B4; B1/B2/B3/B5; B1/B2/B4/B5; B1/B3/B4/B5; B2/B3/B4/B5; and
(e) a combination of five groups of boosters: B1/B2/B3/B4/B5.

The preferred compositions include from about 0.001% to about 10%, by weight of the composition of a retinoid.

The compounds included in the present invention as boosters are selected based on the ability of such compounds to pass, at a certain concentration listed in Table A, in-vitro Assays for a specific enzymes as described below under sections 2.1 through to 2.7. Such a booster is included in the present invention even if it is not explicitly mentioned herein. Put another way, if a compound inhibits or enhances sufficiently an enzyme in an assay described below, it will act in combination with a retinoid to mimic the effect on keratinocytes (skin cells) of retinoic acid, and thus it is included within the scope of the present invention.

The term "conditioning" as used herein means prevention and treatment of dry skin, acne, photo-damaged skin, appearance of wrinkles, age spots, aged skin, increasing stratum corneum flexibility, lightening skin colour, controlling sebum excretion and generally increasing the quality of skin. The composition may be used to improve skin desquamation and epidermal differentiation.

The presence of the selected compounds in the inventive product substantially improves the performance of a retinoid.

The inventive compositions contain, as a preferred ingredient, a retinoid, which is selected from retinyl esters, retinol, retinal and retinoic acid, preferably retinol or retinyl ester. The term "retinol" includes the following isomers of retinol: all-trans-retinol, 13-cis-retinol, 11-cis-retinol, 9-cis-retinol, 3,4-didehydro-retinol, 3,4-didehydro-13-cis-retinol; 3,4-didehydro-11-cis-retinol; 3,4-didehydro-9-cis-retinol. Preferred isomers are all-trans-retinol, 13-cis-retinol, 3,4-didehydro-retinol, 9-cis-retinol. Most preferred is all-trans-retinol, due to its wide commercial availability.

Retinyl ester is an ester of retinol. The term "retinol" has been defined above. Retinyl esters suitable for use in the present invention are $C_1$-$C_{30}$ esters of retinol, preferably $C_2$-$C_{20}$ esters, and most preferably $C_2$, $C_3$, and $C_{16}$ esters because they are more commonly available. Examples of retinyl esters include but are not limited to: retinyl palmitate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecandate, retinyl laurate, retinyl tridecanoate, retinyl myristate, retinyl pentadecanoate, retinyl heptadeconoate, retinyl stearate, retinyl isostearate, retinyl nonadecanoate, retinyl arachidonate, retinyl behenate, retinyl linoleate, and retinyl oleate.

The preferred ester for use in the present invention is selected from retinyl palmitate, retinyl acetate and retinyl propionate, because these are the most commercially available and therefore the cheapest. Retinyl linoleate and retinyl oleate are also preferred due to their efficacy.

Retinol or retinyl ester is employed in the inventive composition in an amount of from about 0.001% to about 10%, preferably in an amount of from about 0.01% to about 1%, most preferably in an amount of from about 0.01% to about 0.5%.

The essential ingredient of the inventive compositions is a compound which passes in vitro Assays described below in sections 2.1 through to 2.7. A compound suitable for use in the present invention inhibits or enhances at a concentration listed in Table A an enzyme to at least a broad % listed in Table A.

Section A: Identification of Booster

TABLE A

Booster Test Concentrations and % Inhibition/Increase

ARAT/LRAT Assay (To identify B1 boosters)

| Invention | Compound Concentration | % Inhibition |
|---|---|---|
| Broad | 100 μM | >10% |
| Preferred | 100 μM | >25% |
| Most Preferred | 100 μM | >40% |
| Optimum | 100 μM | >50% |

Retinol Dehydrogenase Assay (To identify B2 boosters)

| Invention | Compound Concentration | % Increase |
|---|---|---|
| Broad | 100 μM | >10% |
| Preferred | 100 μM | >15% |
| Most Preferred | 100 μM | >20% |
| Optimum | 100 μM | >25% |

Retinal Reductase Assay (To identify B3 boosters)

| Invention | Compound Concentration | % Inhibition |
|---|---|---|
| Broad | 100 μM | >5% |
| Preferred | 100 μM | >10% |
| Most Preferred | 100 μM | >20% |
| Optimum | 100 μM | >35% |

CRABPII Antagonist Assay (To identify B4 boosters)

| Invention | Compound:Retinoic acid Ratio | % Inhibition |
|---|---|---|
| Broad | 7000:1 | >25% |
| Preferred | 7000:1 | >50% |
| Most Preferred | 70:1 | >25% |
| Optimum | 70:1 | >50% |

Retinoic Acid Oxidation Assay (To identify B5 boosters)

| Invention | Compound Concentration | % Inhibition |
|---|---|---|
| Broad | 100 μM | >25% |
| Preferred | 100 μM | >45% |
| Most Preferred | 100 μM | >70% |
| Optimum | 100 μM | >80% |

The in vitro Microsomal Assays employed for determining the suitability of the inclusion of the compound in the inventive compositions are as follows:

1. Materials

All-trans-retinol, all-trans-retinoic acid, palmitoyl-CoA, dilauroyl phosphatidyl choline, NAD, and NADPH were purchased from Sigma Chemical Company. Stock solutions of retinoids for the microsomal assays were made up in HPLC grade acetonitrile. All retinoid standard stock solutions for HPLC analysis were prepared in ethanol, stored under atmosphere of $N_2$ at −70° C. and maintained on ice under amber lighting when out of storage. Other chemicals and the inhibitors were commercially available from cosmetic material suppliers or chemical companies such as Aldrich or International Flavours and Fragrances.

2. Methods 2.1 Isolation of RPE Microsomes (Modified From (1))

50 frozen hemisected bovine eyecups, with the retina and aqueous humor removed were obtained from W. L. Lawson Co., Lincoln, Nebr., USA. The eyes were thawed overnight and the colored iridescent membrane was removed by peeling with forceps. Each eyecup was washed with 2×0.5mL cold buffer (0.1M PO4/1 mM DTT/0.25N sucrose, pH 7) by rubbing the darkly pigmented cells with an artist's brush or a rubber policeman. The cell suspension was added to the iridescent membranes and the suspension was stirred for several minutes in a beaker with a Teflon stir bar. The suspension was filtered through a coarse filter (Spectra/Por 925μ pore size polyethylene mesh) to remove large particles, and the resulting darkly colored suspension was homogenized using a Glas-Col with a motor driven Teflon homogenizer.

The cell homogenate was centrifuged for 30 min. at 20,000 g (Sorvaal model RC-5B centrifuge with an SS34 rotor in 2.5×10cm tubes at 14,000 RPM). The resulting supernatant was subjected to further centrifugation for 60 min. at 150,000 g (Beckman model L80 Ultracentrifuge with an SW50.1 rotor in 13×51 mm tubes at 40,000 RPM). The resulting pellets were dispersed into ~5 mL 0.1M $PO_4$/5 mM DTT, pH 7 buffer using a Heat Systems Ultrasonics, Inc. model W185D Sonifier Cell Disruptor, and the resulting microsomal dispersion was aliquoted into small tubes and stored at −70° C. The protein concentrations of the microsomes were determined using the BioRad Dye binding assay, using BSA as a standard.

2.2 Isolation of Rat Liver Microsomes (4)

Approximately 6 grams of frozen rat liver (obtained from Harlan Sprague Dawley rats from Accurate Chemical and Scientific Corp.) was homogenized in 3 volumes of 0.1M tris/0.1M KCl/1 mM EDTA/0.25M sucrose, pH 7.4 buffer using a Brinkmann Polytron. The resulting tissue suspension was further homogenized in the motor driven Teflon homogenizer described above. The resulting homogenate was successively centrifuged for 30 min. at 10,000 g, 30 min. at 20,000 g, and 15 min. at 30,000 g, and the resulting supernatant was ultra-centrifuged for 80 min. at 105,000 g. The pellet was sonicated in ~5 mL of 0.1M PO4/0.1 mM EDTA/5 mM $MgCl_2$, pH 7.4 buffer as described above and stored as aliquots at −70° C. Protein concentrations were determined as described above.

2.3 Assay for ARAT and LRAT Activity (to Identify B1)

The procedure below was a modification of a method described in the literature (2). The following buffer was prepared and stored at 4° C.: 0.1M $PO_4$/5 mM dithiothreitol, pH 7.0 ($PO_4$/DTT). On the day of the assay, 2 mg BSA per mL of buffer was added to give a $PO_4$/DTT/BSA working buffer. 1 mM retinol substrate was prepared in acetonitrile and stored in amber bottles under nitrogen gas at −20° C. Solutions of 4 mM Palmitoyl-CoA in working buffer (stored in aliquots) and 4 mM dilauroyl phosphatidyl choline in ethanol were prepared and stored at −20° C. Inhibitors were prepared as 10 mM stock solutions in $H_2O$, ethanol, acetonitrile or DMSO. The quench solution was prepared using pure ethanol containing 50 μg/mL butylated hydroxytoluene (BHT), and a hexane solution containing 50 μg/mL BHT was used for the extractions.

To a 2 dram glass vial, the following were added in order: $PO_4$/DTT/BSA buffer to give a total volume of 500 μL, 5 μL acyl donor (4 mM palmitoyl-CoA and/or dilauroyl phosphatidyl choline), 5 μL inhibitor or solvent blank (10 mM stock or further dilutions) followed by approximately 15 μg of RPE microsomal protein (approximately 15 μL of a ~1 mg/mL microsomal protein aliquot). The mixture was incubated for 5 min. at 37° C. to equilibrate the reaction temperature and then 5 μL 1 mM retinol was added. The vials were capped, vortexed for 5 seconds and incubated for 30-90 minutes at 37° C. The reaction was quenched by adding 0.5 mL ethanol/BHT. The retinoids were extracted by adding 3 mL hexane/BHT, vortexing the tubes for several seconds several times and centrifuging the tubes at low speed for 5 min. to quickly separate the layers. The upper hexane layer was removed into a clean vial, and the aqueous layer re-extracted with another 3 mL hexane/BHT, as described above. The hexane layers were combined, and the hexane evaporated by drying at 37° C. under a stream of nitrogen gas on a heated aluminum block. The dried residue was stored at −20° C. until HPLC analysis. The amount of retinyl palmitate and retinyl laurate was quantitated for ARAT and LRAT activity, respectively, by integration of the HPLC signal as described below.

Note that the incubation solution contains 40 μM acyl donor, 100 μM or less inhibitor, 10 μM retinol, approximately 30 μg/mL microsomal protein, and nearly $0.1M\ PO_4$/pH 7/5 mM DTT/2 mg/mL BSA. All steps subsequent to the addition of retinol were done in the dark or under amber lights.

2.4 Assay for Retinol Dehydrogenase Activity (to Identify B2)

The following stock solutions were prepared:
50 mM KH2PO4, pH 7.4 buffer, sterile filtered.
10 mM all trans Retinol (Sigma R7632) in DMSO.
200 mM Nicotinamide adenine dinucleotide phosphate, sodium salt (NADP) (Sigma N0505) in sterile water.
40 mM test compound in appropriate solvent (water, buffer, ethanol, chloroform or DMSO).
1:10 dilution of rat liver Microsomes in 50 mM KH2PO4, pH 7.4 buffer (4 μg/μl).

In a two-dram glass vial with screw cap, the following were added in order:
Buffer to give a final volume of 400 μl
25 μl diluted Microsomes (final=100 μg)—boiled Microsomes were used for controls and regular Microsomes for test samples.
4 μl of 200 mM NADP (final=2 mM)
1 μl of 40 mM test compound (final=100 μM)
8 μl of 10 mM retinol (final=200μM)

The vials were incubated in a 37° C. shaking water bath for 45 minutes. 500 μl ice-cold ethanol was added to each vial to quench the reaction. The retinoids were extracted twice with ice cold hexane (2.7 ml per extraction). Retinyl acetate (5 μl of a 900 μM stock) was added to each vial during the first extraction as a means of monitoring the extraction efficiency in each sample. Samples were vortexed for ten seconds before gently centrifuging for five minutes at 1000 rpm, 5° C. in a Beckman GS-6R centrifuge. The top hexane layer containing the retinoids was removed from the aqueous layer after each extraction to a clean two-dram vial. The hexane was evaporated off under a gentle stream of nitrogen gas. The dried residue was then stored at −20° C. until HPLC analysis.

2.5 Assay for Retinal Reductase Activity (to Identify B3)

All stock solution were prepared as above with the following substitutions:
10 mM all trans Retinaldehyde (Sigma 82500) in DMSO—instead of retinol.
200 mM, Nicotinamide adenine dinucleotide phosphate, reduced form, tetrasodium salt (NADPH) (Sigma N7505) in sterile water—instead of NADP.

In a two-dram glass vial with screw cap, add the following in order:
Buffer to give a final volume of 400 μl
25 μl diluted Microsomes (final=100 μg)—use boiled Microsomes for controls and regular Microsomes for test samples.
4 μl of 200 mM NADPH (final=2 mM)
1 μl of 40 mM test compound (final=100 μM)
3 μl of 10 mM retinaldehyde (final=75 μM)

Follow the same incubation and extraction procedure as detailed above.

2.6 Assay for CRABPII Antagonists (to Identify B4)

2.6.1. Synthesis of CRABPII a. System of Expression

The gene CRABPII was cloned in pET 29a-c(+) plasmid (Novagen). The cloned gene was under control of strong bacteriophage T7 transcription and translation signals. The source of T7 polymerase was provided by the host cell *E.coli* BLR(DE3)pLysS (Novagen). The latter has a chromosomal copy of T7 polymerase under lacUV5 control, induced by the presence of IPTG.

The plasmid was transferred into *E. coli* BLR(DE3)pLysS cells by transformation according to the manufacturer protocol (Novagen).

b. Induction

An overnight culture of the transformed cells was diluted 1:100 into 2×YT containing 50 μg/mL kanamycin and 25 μg/mL chloramphenicol. The cells grew while shaking at 37° C. until the OD at 600 nm reached 0.6-0.8. Then IPTG was added to a final concentration of 1 mM and the culture was incubated for an additional two hours. The cells were harvested by centrifugation at 5,000 g for 10 minutes at room temperature. The pellet was stored at −20° C.

2.6.2. Purification

Purification was performed according to the method described in Norris and Li, 1997.

a. Lysis

The frozen pellet was thawed at RT and resuspended in 1-2 pellet volumes of freshly prepared lysis buffer (50 mM Tris-HCl, pH 8, 10% (w/v) sucrose, 1 mM EDTA, 0.05% (w/v) sodium azide, 0.5 mM DTT, 10 mM $MnCl_2$, 2.5 mM phenylmethylsulfonyl fluoride, 2.5 mM benzamidine, 6 μg/mL DNase). The lysate was incubated for 30 mins. at room temperature. Further lysis was accomplished by sonication (six 30-sec bursts at 10,000 psi alternated with five 30-sec delay on ice). The insoluble fraction of the lysate was removed by centrifugation at 15,000 rpm 1 hour at 4° C. and the supernatant is stored at −20° C.

b. Gel Filtration on Sephacryl S300

The supernatant from step a. was loaded onto a 2.5×100 cm column of sephacryl S-300 (Pharmacia) at room temperature. The elution buffer was 20 mM Tris-HCl, pH 8, 0.5 mM DTT, 0.05% sodium azide (buffer A). The flow rate was 2 mL/min. Collected 2-mL fractions were checked for ultraviolet absorbance at 280 nm. The fractions representing the peaks were examined by SDS-page for the presence of CRABPII.

c. Anion-Exchange Chromatography 2 mL of gel filtration fractions containing CRABPII were loaded onto a quaternary amine anion-exchange column FPLC (Fast Protein Liquid Chromatography) type monoQ (Pharmacia).

CRABPII was eluted using a gradient buffer from 100% buffer A to 30% buffer B (100% buffer B=buffer A+250 mM NaCl) over a 20-min period at room temperature. 1 mL-fractions were collected every minute. Once more, the presence of CRABPII was checked by SDS page. CRABPII was stored at 4° C. before freeze-drying using a Micromodulyo 1.5K with vial platform attachment (Edwards High Vacuum International). The desiccated samples were stored at room temperature until their use in the binding assay.

d. Detection of the Presence of CRABPII

The expression and purification of CRABPII was validated using denaturing SDS-polyacrylamide gel electrophoresis (SDS-PAGE) analysis on a 7-15% polyacrylamide gel (Biorad). 10 µL samples were mixed with 10 µL of 2× loading buffer (100 mM Tris-HCl pH 6.8, 4% SDS, 0.2% BPB, 20% glycerol, 1 mM DTT) and denatured by heating (2 mins. at 80° C.). The samples were loaded onto the gel that was immersed in a 1× Tris-glycine buffer (Biorad) and a constant current (25 mA) was applied for 1 hour at room temperature. After Coomassie blue staining, the protein was identified according to its molecular weight as determined with the Benchmark pre-stained protein ladder (Gibco BRL).

A western blot was used to confirm the presence of CRABPII. The proteins separated on the SDS-PAGE were transferred on an Immobilon-P transfer membrane (Millipore) using a Biorad cassette. The transfer occurred in 1× Tris-glycine buffer (Biorad)+10% methanol. An electrical currant (60 mA) was applied for 3 hours to allow the protein to migrate through the membrane. Afterwards, the membrane was blocked with 5% dry milk in 1×TBS for one hour at room temperature and probed with primary antibodies to CRABPII (1/1000 dilution of mouse anticlonal 5-CRA-B3) in the same buffer at 4° C. overnight. The following day, the membrane was washed with PBS (3×5 minutes) and then incubated with 1:2000 dilution of the secondary antibody, peroxidase conjugated anti-mouse antibody (ECL™, Amersham), for 1 hour at room temperature. The membrane was washed with 1×PBS (3×5 minutes) and the protein was detected using ECL detection kit according to the manufacturer instruction (Amersham).

The concentration of purified CRABPII was determined using BSA kit (Pierce).

2.6.3. Radioactive Binding Assay 220 pmol of CRABPII was incubated in 20 mM Tris-HCl buffer pH 7.4 with 15 pmol of radioactive all trans retinoic acid (NEN) in a total volume of 70 µL. For the competitive assay, another ligand in excess (6670:1, 670:1 or 70:1) was added to the mix. The reaction occurred for one hour at room temperature in the dark. in order to separate the unbound all-trans retinoic acid from the bound all-trans retinoic acid, a 6 kD cut-off minichromatography column (Biorad) was used. The storage buffer was discarded using a Microplex manifold for according to the manufacturer instruction (Pharmacia). The samples were loaded onto the column and the separation occurred by gravity over a 30-min period. Retinoic acid ("RA") bound to CRABPII appeared in the filtrate while free RA remained in the column. The radioactivity of the filtrate was measured by scintillation counter.

2.7 Assay for NADPH Dependent Retinoic Acid Oxidation (to Identify B5)

The procedure below is a modification of a method described in the literature (4). The following assay buffer was prepared and stored at 4° C.: 0.1M $PO_4$/0.1 mM EDTA/5 mM $MgCl_2$, pH 7.4. On the day of the assay, a 60 mM NADPH solution in buffer was prepared. Inhibitor stocks, acidified ethanol/BHT quench solution, and hexane/BHT were prepared as described above. A working 1 mM retinoic acid solution was prepared by dilution of a 15 mM stock (in DMSO) with ethanol.

To a 2 dram vial, the following were added in Order: assay buffer to give a final volume of 500 µL, 20 µL 60 mM NADPH, 5 µL inhibitor or solvent blank, followed by approximately 2 mg of rat liver microsomal protein.

The mixture was incubated for 5 mins. at 37° C., then 5 µL working 1 mM retinoic acid solution was added. Incubation was continued for 60 mins. at 37° C.—the vials were not capped, since the oxidation process required molecular $O_2$ in addition to NADPH. Quenching was carried out with acidified ethanol/BHT and extraction was carried out with hexane/BHT as described above. Quantitation of the quickly eluting polar retinoic acid metabolites (presumed td be 4-oxo retinoic acid) was carried out by integration of the HPLC signal as described below.

All steps subsequent to the addition of retinoic acid were done in the dark or under amber lights. The final incubation solution contained 2.4 mM NADPH, 100 µM or less inhibitor, 10 µM retinoic acid, approximately 4 mg/mL rat liver microsomal protein and nearly 0.1M $PO_4$/0.1 mM EDTA/5 mM $MgCl_2$.

HPLC Analysis of Individual Retinoids

Samples for retinoid quantitation by HPLC were prepared by dissolving the residue in each vial with 100 µL of methanol. The solution was transferred to a 150 µL glass conical tube within a 1 mL shell vial, capped tightly, and placed inside a Waters 715 Autosampler. Aliquots of 60 µL were injected immediately and analysed for retinoid content.

The chromatography instrumentation consisted of a Waters 600 gradient controller/pump, a Waters 996 Photodiode Array detector and a Waters 474 Scanning Fluorescence detector. Two HPLC protocols were used for retinoid analysis. For the ARAT and LRAT assay, the separation of retinol and retinol esters was performed with a Waters 3.9×300 mm C18 Novapak reverse-phase analytical column and Waters Sentry NovaPak C18 guard column with an 80:20 (v/v) methanol/THF isocratic mobile phase adjusted to a flow rate of 1 mL/min. for 10 min. The eluate was monitored for absorbance at 325 nm and fluorescence at 325 ex/480 em.

A shorter Waters 3.9×150 mm C18 Novapak reverse-phase analytical column and Waters Sentry NovaPak C18 guard column were used to separate retinoid acids and alcohols for the retinol and retinoic acid oxidation assays utilising a modification of a gradient system described by Barua (5). This system consisted of a 20 mins. linear gradient from 68:32 (v/v) methanol/ water containing 10 mM ammonium acetate to 4:1 (v/v) methanol:dichloromethane followed by a 5 mins. hold at a flow rate of 1 mL/min. The column eluate was monitored from 300 nm to 400 nm.

These protocols were selected based on their ability to clearly resolve pertinent retinoid acids, alcohols, aldehydes, and/or esters for each assay and relative quickness of separation. Identification of individual retinoids by HPLC was based on an exact match of the retention time of unknown peaks with that of available authentic retinoid standards and UV spectra analysis (300-400 nm) of unknown peaks against available authentic retinoids.

References

1 J. C. Saari & D. L. Bredberg, "CoA and Non-CoA Dependent Retinol Esterification in Retinal Pigment Epithelium", J. Bill. Chem. 263, 8084-8090 (1988).

2 J. C. Saari & D. L. Bredberg, "ARAT & LRAT Activities of Bovine Retinal Pigment Epithelial Microsomes", Methods Enzymol. 190, 156-163 (1990).
3 J. L. Napoli & K. R. Race, "The Biosynthesis of Retinoic Acid from Retinol by Rat Tissues in vitro", Archives Biochem. Biophys. 255, 95-101 (1987).
4 R. Martini & M. Murray, "Participation of P450 3A Enzymes in Rat Hepatic Microsomal Retinoic Acid 4-Hydroxylation", Archives Biochem. Biophys. 303, 57-66 (1993).
5 A. B. Barua, "Analysis of Water-Soluble Compounds: Glucuronides", Methods Enzymol. 189, 136-145 (1990).

The boosters suitable for use in the present invention include but are not limited to the boosters listed in Tables $B_1$ through to $B_5$ below. The table below gives the booster class ($B_1$-$B_5$), the chemical name of the compound, and the results from the appropriate assays used to identify the booster (i.e. ARAT/LRAT for B1, retinol dehydrogenase for $B_2$, retinaldehyde inhibation for B3, CRABP is binding for $B_4$ and retinoic acid oxidation inhibition for $B_5$.

| ARAT/LRAT Inhibitors (B1) | | | | | | | |
|---|---|---|---|---|---|---|---|
| Class | Compound | % Inhibition Overall TG (−ROH/RE) | Overall TG (IC 50) | % Inhibition ARAT (10 μm) | % Inhibition ARAT (100 μm) | % Inhibition LRAT (10 μm) | % Inhibition LRAT (100 μm) |
| Carotenoid | Crocetin | | 3.75E−05 | 15% | 34% | 0 | 15% |
| Fatty Acid & Other Surfactants | Acetyl Sphingosine | | 6.78E−06 | 19% +/− 12 | 62% +/− 11 | 10% +/− 10 | 50% +/− 18 |
| Fatty Acid Amides & Other Surfactants | C13 Beta-Hydroxy Acid/Amide | 17% | | | 28% | | 25% |
| Fatty Acid Amides & Other Surfactants | Castor Oil MEA | | 3.25E−05 | | | | |
| Fatty Acid Amides & Other Surfactants | Cocamidopropyl Betaine | | | | 25% | | |
| Fatty Acid Amides & Other Surfactants | Coco Hydroxyethylimidazoline | | 2.84E−07 | | 68% | | 68% |
| Fatty Acid Amides & Other Surfactants | Cocoamide-MEA (or Cocoyl Monoethanolamide) | 11% | | | 13% | | 34% |
| Fatty Acid Amides & Other Surfactants | Glycerol-PCA-Oleate | | | | 41% +/− 6 | | 58% +/− 2 |
| Fatty Acid Amides & Other Surfactants | Hexanoamide | | | | 20% | | |
| Fatty Acid Amides & Other Surfactants | Hexanoyl Sphingosine | | 9.99E−05 | | 28% +/− 4 | | 37% +/− 9 |
| Fatty Acid Amides & Other Surfactants | Hydroxyethyl-2-Hydroxy-C12 Amide | | 3.29E−05 | | 35% | | 35% |
| Fatty Acid Amides & Other Surfactants | Hydroxyethyl-2-Hydroxy-C16 Amide | | | | 25% | | 30% |
| Fatty Acid Amides & Other Surfactants | Lauroyl Sarcosine | | | | 20% | | |
| Fatty Acid Amides & Other Surfactants | Lidocaine | | | | 12% | | 0 |
| Fatty Acid Amides & Other Surfactants | Linoleamide-DEA (or Linoleoyl Diethanolamide) | 59% | | 12% +/− 3 | 43% +/− 3 | 11% +/− 9 | 51% +/− 15 |
| Fatty Acid Amides & Other Surfactants | Linoleamide-MEA (or Linoleoyl Monoethanolamide) | | 1.61E−05 | 14% | 35% | 20% +/− 8 | 35% |
| Fatty Acid Amides & Other Surfactans | Linoleamidopropyl Dimethylamine | | | | 69% +/− 18 | | 75% +/− 4 |
| Fatty Acid Amides & Other Surfactants | Melinamide | | | | 64% +/− 15 | | 43% +/− 21 |
| Fatty Acid Amides & Other Surfactans | Myristoyl Sarcosine | | | | 41% +/− 14 | | 11% +/− 11 |
| Fatty Acid Amides & Other Surfactants | Oleyl Betaine | | 2.80E−05 | | 47% | | |
| Fatty Acid Amides & Other Surfactants | Palmitamide-MEA | | | 6% | 23% | 12% | 33% |
| Fatty Acid Amides & Other Surfactants | Stearylhydroxyamide | | | | 10% | | 10% |
| Fatty Acid Amides & Other Surfactants | Utrecht-1 | 21% | | 43% | 54% | 51% | 48% +/− 6 |
| Fatty Acid Amides & Other Surfactants | Utrecht-2 | | 3.47E−06 | 42% | 83% +/− 9 | 51% | 92% +/− 3 |
| Flavanoids | Naringenin | | | | 33% | | 14% |
| Fragrances | Allyl Alpha-Ionone | | | 16% +/− 14 | 22% +/− 23 | 17% +/− 10 | 36% /− 7 |
| Fragrances | Alpha-Damascone | | 3.35E−04 | 67% +/− 27 | 83% +/− 12 | 87% +/− 6 | 98% +/− 1 |
| Fragrances | Alpha-Ionone | | 9.27E−04 | | 45% +/− 27 | | 49% +/− 30 |
| Fragrances | Alpha-Methyl Ionone | | | | 67% | | 77% |
| Fragrances | Alpha-Terpineol | | | | 26% | | 25% |
| Fragrances | Beta-Damascone | | | 45% | 84% | 52% | 92% |
| Fragrances | Brahmanol | | | | 70% | | 75% |
| Fragrances | Damascenone | | | 23% | 70% | 29% | 79% |
| Fragrances | Delta-Damascone | | | 58% | 87% | 64% | 95% |
| Fragrances | Dihydro Alpha-Ionone | | | | 13% | | 18% |
| Fragrances | Ethyl Saffranate | | | | 51% | | 49% |
| Fragrances | Fenchyl Alcohol | | | | 12% | | 4% |
| Fragrances | Gamma-Methyl Ionone | | | | 21% | | 38% |

-continued

ARAT/LRAT Inhibitors (B1)

| Class | Compound | % Inhibition Overall TG (−ROH/RE) | Overall TG (IC 50) | % Inhibition ARAT (10 μm) | % Inhibition ARAT (100 μm) | % Inhibition LRAT (10 μm) | % Inhibition LRAT (100 μm) |
|---|---|---|---|---|---|---|---|
| Fragrances | Isobutyl Ionone | | | | 8% | | 45% |
| Fragrances | Isocyclogeraniol | | | | 18% | | 16% |
| Fragrances | Isodamascone | | | | 80% | | 92% |
| Fragrances | Lyral | | 1.27E−04 | | 76% | | 71% |
| Fragrances | Santalone | | | | 23% | | 12% |
| Fragrances | Santanol | | | | 15% | | 43% |
| Fragrances | Timberol | | | | 34% | | 33% |
| Fragrances | Tonalid | | | | 50% | | 33% |
| Fragrances | Traseolide | | | | 41% | | 21% |
| Miscellaneous | Coco Trimethylammonium Cl- | | | | 27% | | |
| Miscellaneous | Urosolic Acid | | 1.46E−06 | | 21% | | 28% |
| Noncyclic Fragrances | Citral | | | | 20% | | |
| Noncyclic Fragrances | Citronellol | | | | 30% | | 0 |
| Noncyclic Fragrances | Farnesol | | 9.35E−05 | 23% +/− 18 | 53% +/− 18 | 10% +/− 7 | 53% +/− 19 |
| Noncyclic Fragrances | Geraniol | | 7.83E−03 | 13% | 32% | | |
| Noncyclic Fragrances | Geranyl Geraniol | | | 38% +/− 12 | 81% +/− 6 | 16% +/− 9 | 77% +/− 13 |
| Noncyclic Fragrances | Linalool | | | | 28% | | 0 |
| Noncyclic Fragrances | Nonadieneal | | | | 20% | | |
| Noncyclic Fragrances | Pseudoionone | | | | 12% | | 37% |
| Phospholipid | Dioctylphosphatidyl Ethanolamine | | | 23% | 50% +/− 2 | 0 | 17% +/− 17 |
| Urea | Dimethyl Imidazolidinone | 22% | | | | | |
| Urea | Imidazolidinyl Urea | 35% | | | | | |

Retinol Dehydrogenase Activators (B2)

| Class | Compound | % Increase Retinol Dehydrogenase |
|---|---|---|
| Phospholipid | Phosphatidyl Choline | 21% increase |
| Phospholipid | Sphingomyelin | 26% increase |

Retinaldehyde Reductase Inhibitors (B3)

| Class | Compound | Overall TG(IC 50) | % Inhibition Retinal Reductase |
|---|---|---|---|
| Aldehyde | Vanillin | 9.70E−03 | 6% |
| Fatty Acid | Arachidic Acid | | 20% |
| Fatty Acid | Arachidonic Acid | | 49% |
| Fatty Acid | Linoleic Acid | 1.63E−04 | 62% +/− 2 |
| Fatty Acid | Linolenic Acid | 1.34E−04 | 54% +/− 16 |
| Fatty Acid | Myristic Acid | 1.72E−05 | 26% |
| Miscellaneous | Amsacrine | 6.26E−06 | 22% +/− 8 |
| Miscellaneous | Carbenoxolone | 3.61E−07 | 26% +/− 2 |
| Miscellenous | Glycyrretinic Acid | 8.64E−06 | 38% +/− 1 |
| Phospholipid | Phosphatidyl ethanolamine | | 37% |

CRABPII Antagonists (B4)

| Class | Compound | Overall TG (IC 50) | % Inhibition CRABPII |
|---|---|---|---|
| Fatty Acid | Elaidic Acid | 6.50E−05 | >50% |
| Fatty Acid | Hexadecanedioic Acid | 1.30E−04 | >50% |
| Fatty Acid | 12-Hydroxystearic Acid | 2.91E−05 | >50% |
| Fatty Acid | Isostearic Acid | 6.88E−05 | >50% |
| Fatty Acids | Linseed Oil | | >50% |

Retinoic Acid Oxidation Inhibitors (B5)

| Class | Compound | Overall TG(IC 50) | % Inhibition Retinoic Acid (10 μM) | % Inhibition Retinoic Acid (100 μM) |
|---|---|---|---|---|
| Imidazole | Bifonazole | | 89% | 100% |
| Imidazole | Climbazole | 4.47E−06 | 80% | 92% |
| Imidazole | Clotrimazole | | 76% | 85% |
| Imidazole | Econazole | | 88% | 100% |
| Imidazole | Ketoconazole | 1.85E−07 | 84% | 84% |
| Imidazole | Miconazole | 2.78E−07 | 74% | 86% |
| Fatty Acid Amides & Other Sufactants | Lauryl Hydroxyethylimidazoline | 4.67E−07 | | |
| Fatty Acid Amides & Other Sufactants | Oleyl Hydroxyethylimidazoline | 3.02E−05 | 54% | 80% |

Retinoic Acid Oxidation Inhibitors (B5)

| Class | Compound | Overall TG(IC 50) | % Inhibition Retinoic Acid (10 µM) | % Inhibition Retinoic Acid (100 µM) |
|---|---|---|---|---|
| Flavanoids | Quercetin | 6.29E−05 | 40% | 74% |
| Coumarin | Coumarin | | | |
| Quinoline | (7H-Benzimidazo [2,1-a]Benz[de]-Isoquinolin-7-one | 8.59E−07 | | |
| Quinoline | Hydroxyquinoline (Carbostyril) | 3.64E−04 | | |
| Quinoline | Metyrapone (2-Methyl-1,2-di-3-Pyridyl-1-Propane) | | | 47% |

Section B. Effects of Booster Combinations

In order to assess the effect of combinations of booster molecules an assay is required which encompasses the effect of each of the five booster classes. A single enzyme assay is not suitable for this purpose, as it will be specific Only for one class of booster molecule. An assay which reflects retinoid concentration in keratinocytes is necessary to relate the effects of single booster molecules with combination of booster molecules. For this reason, a transglutaminase (Tgase) assay was utilised. Tgases are calcium dependent enzymes that catalyse the formation of covalent cross-links in proteins. Several Tgase enzymes are membrane bound in keratinocytes which is important for epidermal cell maturation. This enzyme is inhibited by retinoic acid. The higher the concentration of retinoic acid, the greater the inhibition of Tgase expression. Hence Tgase is a good marker of both keratinocyte differentiation and of the retinoid effect on keratinocytes.

Transglutaminase as a Marker of Skin Differentiation

During the process of terminal differentiation in the epidermis, a 15 nm thick layer of protein, known as the cornified envelope (CE) is formed on the inner surface of the cell periphery. The CE is composed of numerous distinct proteins which have been cross-linked together by the formation of N$\Sigma$-($\gamma$-glutamyl) lysine isodipeptide bonds catalysed by the action of at least two different transglutaminases (TGases) expressed in the epidermis. TGase I is expressed in abundance in the differentiated layers of the epidermis, especially the granular layer, but is absent in the undifferentiated basal epidermis. Thus TGase I is a useful marker of epidermal keratinocyte differentiation with high TGase I levels indicating a more differentiated state. An ELISA based TGase I assay, using a TGase I antibody, was used to assess the state of differentiation of the cultured keratinocytes in the examples that follow.

Keratinocytes (cultured as described above) were plated in 96 well plates at a density of 4,000-5,000 cells per well in 200 µl media. After incubation for two to three days, or until cells are ~50% confluent, the media was changed to media containing test compounds (five replicates per test). The cells were cultured for a further 96 hours after which time the media was aspirated and the plates stored at −70° C. Plates were removed from the freezer, and the cells were washed twice with 200 µl of 1×PBS. The cells were incubated for one hour at room temperature (R/T) with TBS/5% BSA (wash buffer, bovine serum albumin). Next the TGase primary antibody was added: 50 µl of monoclonal anti-Tgase I Ab B.C. diluted 1:2000 in wash buffer. The primary antibody was incubated for 2 hours at 37° C. and then rinsed 6× with wash buffer. Cells were then incubated with 50 µl of secondary antibody (Fab fragment, peroxidase conjugated anti-mouse IgG obtaining from Amersham) diluted 1:4,000 in wash buffer for two hours at 37° C., then rinsed three times with wash buffer. Following the rinse with washing buffer, the cells were rinsed 3× with PBS. For colourimetric development, the cells were incubated with 100 µl substrate solution (4 mg o-phenylenediamine and 3.3 µl 30% $H_2O_2$ in 10 ml 0.1M citrate buffer pH 5.0) for exactly five minutes, R/T, in darkness (under aluminum foil). The reaction was stopped by the addition of 50 µl 4N $H_2SO_4$. The absorbance of samples was read at 492 nm in a 96 well plate UV spectrophotometer. Out of the five replicates, four were treated with both antibodies, the fifth one was use as a Tgase background control. TGase levels were determined and expressed as percentage control.

Details of Tgase Assay:

Prior to initiating experiments, to determine the effects of combinations of booster molecules standard Tgase assay conditions were investigated. A fully validated Tgase assay was established as follows:

A. Reagents

| | |
|---|---|
| Cells: Human Keratinocytes (P2 in T75 flasks; P3 in 96 well assay plates) | Neonatal Human foreskin |
| Primary Antibody: TGm specific monoclonal Ab B.C1 | Biogenesis (Cat# 5560-6006) |
| Secondary Ab: Peroxidase labeled antimouse Ig F(ab) 2 | Amersham (Cat # NA9310) |
| Substrate solution: For 10 ml phosphate citrate buffer | |
| 4.0 mg o-phenylenediamine | Sigma P-7288 |
| 3.3 µl of 30% $H_2O_2$ | Sigma H-1909 |

B. Media/Buffers

| | |
|---|---|
| Keratinocyte Growth Media (KGM) | Clonetics (Cat# 3111) |
| Phosphate Buffered Saline; Dulbecco's without Ca/MgCl$_2$) | Life Technology (Cat # 14200-075) |
| Tris Buffered Saline | BioRad (Cat #170-6404) |
| Blocking buffer (1xTBS + 5% dry milk) | Sigma (Cat # P-7949) |
| Washing buffer (1% dry milk in TBS + 0.05% Tween 20) | Sigma (Cat # S-9763) |
| Phosphate citrate buffer: 1:1 mixture of 0.2M dibasic sodium phosphate and 0.1M citric acid | Sigma (Cat # C-1909) |
| 4N $H_2SO_4$ | |

C. Culture Ware

| 96-well polypropylene microtitre plate | Costar (Cat # 3595) |
|---|---|
| 96-well polypropylene U-bottom plate | Costar (Cat # 3794) |
| T75-vent cap | Costar (Cat # 3376) |

D: Instrumentation/Equipment

| Biotek Model EL 340 Microplate reader | Bio-tek Instuments Inc. |
|---|---|
| Multiprobe II | Packard |

E: Cell Culture Procedure
Seeding of Keratinocytes in 96 Well Plates
1. A suspension of keratinocytes was prepared at a concentration of 3000 cells/200 µl/ well in KGM medium (Used $3 \times 10^5$ cells/12 ml media in each microtitre plate)
2. 200 µl of the keratinocyte suspension was transferred into each of the inner 60 wells only.
3. 200 µl of KGM media was pipetted into the outer wells (to maintain thermal equilibrium).
4. Each plate was incubated at 37° C. and 5% $CO_2$ for 3 days or until cells are ~50% confluent.
Treatment of Keratinocytes with Samples.
5. Stock solutions of the samples were prepared in DMSO.
6. The samples were diluted to desired concentration with the final assay concentration of DMSO being 0.1%.
7. 20 µl of the sample was transferred into wells and 180 µl of KGM medium added to give a final assay volume of 200 µl.
8. Plates were incubated at 37° C. and 5% $CO_2$ for 72 hours.
9. Media were completely removed from each well.
10. Wells were rinsed with 2× with 200 µl of 1×PBS
11. Finally they were frozen for at least 1.5 hours at −70° C.
F: Transglutaminase Assay
1. Block:
  Incubate plates at room temperature with 200 µl/well of blocking buffer for 1 hour.
2. Primary Antibody:
  Aspirate blocking buffer. Incubated with 100 µl/well of TGm-specific monoclonal antibody B.C1 (diluted 1:2000 in washing buffer) at 37° C. for at least 2 hours. The primary antibody was not added in background control wells.
3. Rinsed wells 6× with washing buffer.
4. Secondary Antibody:
  Incubated with 100 µl/well peroxidase labeled anti-mouse IgF(ab)2 fragment (diluted 1:4000 in washing buffer) at 37° C. for 2 hours.
5. Rinsed wells 3× with washing buffer (added 200 µl) and aspirated after each rinse.
6. Rinsed wells 3× with PBS w/o Tween.
7. Incubated with 100 µl/well substrate solution at room temperature for exactly 5 minutes.
8. Stopped reaction with 50 µl/well 4N $H_2SO_4$.
9. Read absorbance at 492 nm in the Bio-tek plate reader.
I. Optimization Studies
a. Time Course of Transglutaminase Production
A time course experiment was conducted to determine the optimal incubation time for transglutaminase production in keratinocytes grown in 96-well plates (4000 cells/well). This time course study was conducted with multiple variables including dose response analyses of retinoic acid and retinol as well as incubation in the presence of 1.2 mM $CaCl_2$. Although the transglutaminase production in the control cells (0.1% DMSO) was not altered, both retinoic acid and retinol exhibited a dose dependent inhibition of transglutaminase production over the five day incubation period. The most pronounced retinoid effect was observed on day 2 and day 3. The maximal inhibition was observed on day 2 with the transglutaminase production being inhibited by 85% and 55% in the presence of the highest concentration (1 µM) of retinoic acid and retinol respectively. The same experiment was also conducted with varying cell density (3000 cells/well and 5000 cells/well) and comparable results were observed.
B: DMSO Sensitivity
Various concentrations of DMSO ranging from 0-2% were tested for the effect on transglutaminase production in keratinocytes. The assay was sensitive to DMSO concentration with significant inhibition of activity, above 0.5% DMSO. Hence, a final assay concentration of 0.1% was selected for subsequent sample concentration studies.
C: Dose Response Curves: Retinoic Acid and Retinol
Based on the data, day 3 was selected as the optimal time and 0.1% DMSO was selected as the concentration to be used for further testing. An additional dose response experiment was carried out with retinoic acid and retinol in the presence of 0.1% DMSO, with the transglutaminase production being assayed on day 3. A good dose response was observed for Tgase inhibition by retinoic acid and retinol. 10-7M retinol gave an inhibition of Tgase in the linear range of concentration. Therefore, this concentration of retinol was chosen to evaluate the booster combinations.
D: Final Conditions Used to Test Boosters or Combination of Boosters

| Days of incubation of keratinocytes with retinol and boosters | 3 days |
|---|---|
| Final DMSO concentration | less than 0.1% |
| Retinol concentration | 10-7M (0.1 µM) |
| Booster concentrations | 10 mM to 0.1 nM |

Using the above conditions, dose response for all the different boosters (B1-B5) were tested to identify the best concentration of booster to test in combinations.
Transglutaminase levels were determined and expressed in the Tables B1 through B5 either as:
(i) % (booster+retinol inhibition/control inhibition)−% (ROH inhibition/control inhibition), which measures the added effect of booster+retinol induced TGase inhibition over retinol alone, or
(ii) as an IC50 value when the inhibitory effect of multiple booster concentrations was examined—this provides the concentration of booster which, in combination with a constant retinol concentration of $10^{-7}$ M, inhibits TGase by 50%.
Booster Combinations and Booster Ratios:
It has been discovered surprisingly that certain compounds increase the endogenous levels of retinoic acid formation from retinol or retinyl esters by different mechanisms. These compounds are collectively called here as "retinoid boosters". These include: inhibitors of ARAT/LRAT (B1 boosters), inhibitors of retinaldehyde reductase (B3 boosters), inhibitors of retinoic acid binding to CRABP-2 (B4 boosters) and inhibitors of retinoic acid oxidation catalysed by cytochrome P450 enzymes (B5 boosters), or certain other compounds which enhance or activate retinol dehydrogenase (B2 boosters). These boosters are coded as groups B1 through to B5, as seen in chart 1 herein above.

The boosters alone or in combination with each other, potentiate the action of a retinoid by increasing the amount of retinol available for conversion to retinoic acid and inhibiting the degradation of retinoic acid. The boosters act in conjunction with a retinoid (e.g. retinol, retinyl ester, retinal, retinoic acid) the latter being present endogenously in the skin. The preferred compositions, however, include a retinoid in the composition, co-present with a booster, to optimise performance.

The present invention includes, in part, a second composition containing from about 0.0001% to about 50%, preferably from 0.001% to 10%, most preferably from 0.001% to 5% by weight of the composition of at least one booster compound, or a combination of binary, tertiary, quaternary or 5 booster combinations. The combined concentration of the booster combinations of 0.001% to 5% in specified ratios as shown below, inhibit transglutaminase in an in vitro transglutaminase assay to more than 50%, and a cosmetically acceptable vehicle.

The boosters included in the inventive compositions are selected from the group consisting of:
a. Two boosters, wherein both are selected from the group consisting of B2, B3 and B4;
b. Binary combinations of boosters selected from the group consisting of B1/B2; B1/B3, B1/B4; B1/B5; B2/B3, B2/B4; B2/B5; B3/B4, B3/B5; B4/B5
c. Ternary combinations of boosters selected from the group consisting of B1/B2/B3; B1/B2/B4; B1/B2/B5; B1/B3/B4; B1/B3/B5; B1/B4/B5; B2/B3/B4; B2/B3/B5; B2/B4/B5; B3/B4/B5
d. Quaternary combinations of boosters selected from the group consisting of B1/B2/B3/B4; B1/B2/B3/B5; B1/B2/B4/B5; B1/B3/B4/B5; B2/B3/B4/B5; and
e. A combination of five groups of boosters B1/B2/B3/B4/B5.

Booster to Booster Ratios:

The boosters of different classes (B1 to B5) in combinations as shown above have an optimal concentration of between 0.001% to 5% in a cosmetic product at specific ratios as shown below for inhibition of Tgase activity to at least below 50%:

| Invention | Ratios of boosters to boosters | Concentrations |
|---|---|---|
| Broad | 1:10,000 to 10,000:1 | 100 mM to 1 nM |
| Preferred | 1:1000 to 1000:1 | 10 mM to 10 nM |
| Most preferred | 1:100 to 100:1 | 1 mM to 100 nM |
| Optimum | 1:10 to 10:1 | 0.1 mM to 1 μM |

Retinoid to Booster Ratios:

The preferred composition includes a retinoid (e.g.retinol, retinyl ester, and retinaldehyde) in the composition, co-present with a booster or a combination of the boosters, to optimise performance.

For optimum performance, the concentration of retinoid to booster should be present in the composition in ratios as given below:

| Invention | Ratios of boosters to retinoids | Concentrations |
|---|---|---|
| Broad | 10,000:1 to 1:10,000 | 100 mM-1 nM booster; 0.001-10% retinoids |
| Preferred | 1000:1 to 1:1000 | 10 mM-10 nM booster; 0.001-10% retinoid |
| Most preferred | 100:1 to 1:100 | 1 mM-100 nM booster; 0.01-1% retinoid |

Concentrations of Individual Boosters Used in the Examples:

Since the objective is to establish synergistic inhibition of transglutaminase expression by combinations of the active compounds with retinol, it was essential to determine the dose response profiles ($IC_{20}$ and $IC_{50}$ values) of the active compounds, when tested individually in the presence of retinol. The detailed dose response of boosters belonging to B2-B4 is given in the tables following the IC50 and IC 20 table below. This data was used to identify an appropriate sub-maximal inhibitory concentration of each active compound, to eventually make it possible to identify putative synergistic effects of the mixtures of the active compounds in the presence of retinol. The data in the following table represents the $IC_{50}$ and $IC_{20}$ (80% of control) values and the concentrations used when testing synergies with combinations of boosters.

In order to demonstrate synergy of two compounds, it is essential to select concentrations to test that are at most IC20, in other words, a compound concentration that individually boosts the retinol inhibition of Tgase expression by 20%. Two such compounds should have an additive inhibition of 40%. Using this strategy to determine concentrations leaves a window of 40-100% for further inhibition for detecting synergy of the two compounds under examination.

A more challenging concentration criterion would be selecting concentrations of compounds which alone showed no inhibition effect, but in combination show inhibition. In this study however, we chose an even more challenging criteria. We selected concentrations of compounds that were 10 to 1000 fold lower than the minimally effective Tgase inhibiting, concentration. Identification of synergistic combinations using such very low concentrations would mean that the most effective synergistic combinations were identified.

| Booster Class | Compound Name | $IC_{50}$ | $IC_{20}$ | Con. Used for synergy (binary, tertiary, quaternary) |
|---|---|---|---|---|
| B1 | LinoleoylMonoethanolamide (LAMEA) | 1.61E−05 | 1.48E−05 | 1E−05 to 1E−09 |
| | Palmitamide Monoethanolamide | ND | ND | 1E−06 to 1E−10 |
| | Oleyl Betaine | 2.80E−05 | 1.08E−05 | 1E−05 to 1E−8 |
| | Naringenin | ND | ND | 1E−05 to 1E−09 |
| | *Echinacea* | ND | ND | 1E−05 to 1E−09 |
| | Dimethyl imidazolinone | ND | ND | 1E−05 to 1E−09 |
| | Melinamide | ND | ND | 1E−05 to 1E−09 |
| | Geranyl geraniol | ND | ND | 1E−05 to 1E−09 |

-continued

| Booster Class | Compound Name | IC$_{50}$ | IC$_{20}$ | Con. Used for synergy (binary, tertiary, quaternary) |
|---|---|---|---|---|
| | Farnesol | 9.35E−05 | 7.82E−05 | 1E−06 to 1E−09 |
| | Geraniol | 7.83E−03 | 4.72E−03 | 1E−03 to 1E−07 |
| | α-Damascone | 3.35E−04 | 1.69E−04 | 1E−04 to 1E−08 |
| | α-Ionone | 9.27E−04 | 1.42E−04 | 1E−04 to 1E−08 |
| | Castor oil Methyl Ester Acid (MEA) | 3.25E−05 | 9.38−E06 | 1E−06 to 1E−09 |
| | Ursolic Acid | 1.46E−06 | 5.94−E07 | 1E−06 to 1E−09 |
| | Utrecht-2 | 3.47−E06 | 3.30−E06 | 1E−06 to 1E−09 |
| | Cocoyl hydroxyethylimidazoline | 2.84E−07 | 9.21E−08 | 1E−08 to 1E−11 |
| | Acetyl sphingosine (C2 Ceramide) | 6.78E−06 | 5.15E−06 | 1E−06 to 1E−09 |
| | Hexanoyl sphingosine (C6 Ceramide) | 9.99E−05 | 6.94E−05 | 1E−05 to 1E−09 |
| | Crocetin | 3.75E−05 | 2.52E−05 | 1E−05 to 1E−09 |
| | Lyrial | 1.27E−04 | 4.00E−05 | 1E−05 to 1E−09 |
| | N-Hydroxyethyl-2-hydroxydodecyl amide | 3.29E−05 | 2.40E−05 | 1E−05 to 1E−09 |
| B2 | Phosphatidyl Choline | ND | ND | 1E−05 to 1E−09 |
| | Sphingomyelin | ND | ND | 1E−05 to 1E−09 |
| | TCC | 9.64E−07 | 6.18−E07 | 1E−07 to 1E−10 |
| | 1,2-dioctanoyl-sn-glycero-3-phosphoethanolamide | ND | ND | 1E−05 to 1E−09 |
| B3 | Amsacrine-HCl | 6.26E−06 | 3.30E−06 | 1E−06 to 1E−09 |
| | Carbenoxolone | 3.61E−07 | 2.00E−07 | 1E−07 to 1E−10 |
| | Glycyrrhetinic Acid | 8.64E−06 | 5.96E−06 | 1E−06 to 1E−09 |
| | Linoleic Acid | 1.63E−04 | 8.95E−05 | 1E−05 to 1E−09 |
| | Linolenic Acid | 1.34E−04 | 1.21E−04 | 1E−05 to 1E−09 |
| | Arachidonic Acid (Na+ salt) | ND | ND | 1E−05 to 1E−09 |
| | Myristic Acid | 1.72E−05 | 1.05E−05 | 1E−05 to 1E−09 |
| | Vanilin | 9.70E−03 | 8.47E−03 | 1E−03 to 1E−06 |
| B4 | Hexadecanedioic acid | 1.30E−04 | 8.40E−05 | 1E−05 to 1E−09 |
| | 12-Hydroxystearic acid | 2.91E−05 | 1.45E−05 | 1E−05 to 1E−09 |
| | Elaidic acid | 6.50E−05 | 5.88E−05 | 1E−05 to 1E−09 |
| | Linseed oil | ND | ND | 1E−05 to 1E−09 |
| | Isostearic acid | 6.88E−05 | 6.23E−05 | 1E−05 to 1E−09 |
| | 2-Hydroxystearic acid | ND | ND | 1E−05 to 1E−09 |
| B5 | Climbazole | 4.47E−06 | 2.45E−07 | 1E−07 to 1E−10 |
| | Clotrimazole | ND | ND | 1E−05 to 1E−09 |
| | Miconazole | 2.78E−07 | 8.42E−08 | 1E−08 to 1E−11 |
| | Coumarin | ND | ND | 1E−05 to 1E−09 |
| | Ketoconazole | 1.85E−07 | 5.52E−08 | 1E−08 to 1E−11 |
| | 3,4,-Dihydro-2(1H)-quinolinone (Hydrocarbostyril) | ND | ND | 1E−05 to 1E−09 |
| | 2-Hydroxyquinoline (Carbostyril) | 3.64E−04 | 1.70E−04 | 1E−04 to 1E−08 |
| | Amino Benzotriazole | ND | ND | 1E−05 to 1E−09 |
| | Lauryl hydroxyethylimidazoline | 4.67E−07 | 2.69E−07 | 1E−07 to 1E−10 |
| | Quercetin | 6.29E−05 | 5.11E−05 | 1E−05 to 1E−09 |
| | Oleoyl hydroxyethlimidazoline | 3.02E−05 | 5.65E−06 | 1E−06 to 1E−09 |
| | 7H-Benzimidazo[2,1-a]Benz[de]-isoquinolin-7-one | 8.59E−07 | 4.69E−07 | 1E−07 to 1E−09 |

ND: Not determined or a clear dose response was not observed. For synergies, a wide range of concentration (4 orders of magnitude 10-5 to 10-9M) was tested.

Dose Response for Boosters Class B2 to B4

The following tables include the data on the dose response of boosters belonging to class B2 to B4. Concentration of boosters are given in Molar; mean Tgase level and Standard deviation of 4 replicates is expressed as % of control (0.1% DMSO and $10^{-7}$M retinol). Higher numbers (close to 100 or above 100) indicate no inhibition of Tgase. The lower the number, the more potent the inhibitor is at that concentration. The IC 50 and IC20 values were calculated from this dose response table and expressed in the above table.

B2 Class Boosters

| Concentration | Tgase levels (Mean) | Tgase (SD) |
|---|---|---|
| Phosphatidyl choline (B2) | | |
| 4.4E−05 | 90.9 | 0.01 |
| 1.47E−05 | 120.3 | 10.6 |
| 4.89E−06 | 70.1 | 11.4 |
| 1.63E−06 | 98.8 | 0.00 |
| 5.43E−07 | 86.7 | 6.19 |
| 1.8E−07 | 75.9 | 20.5 |
| 6.0E−08 | 87.8 | 3.9 |
| 1.2E−08 | 159 | 42.3 |
| 2.4E−09 | 85.5 | 0.39 |
| Sphingomyelin (B2) | | |
| 3.0E−05 | 45 | 3.21 |
| 1.0E−05 | 77.8 | 25.5 |
| 3.33E−06 | 76.4 | 7.55 |
| 1.1E−06 | 98.8 | 0.00 |
| 3.73E−07 | 91.6 | 14.9 |
| 1.23E−07 | 70.0 | 3.63 |
| 4.10E−08 | 74.6 | 4.19 |
| 8.2E−08 | 115.2 | 1.02 |
| 1.65E−09 | 68.4 | 2.03 |
| 3.29E−10 | 69.2 | 2.1 |
| TCC (B2) | | |
| 1.14E−03 | 36.3 | 4.6 |
| 3.8E−04 | 3.8 | 0.96 |
| 3.31.23E−04 | −3.2 | 0.91 |
| 4.22E−05 | −11.2 | 0 |
| 1.41E−06 | −.3 | 4.88 |
| 4.69E−07 | 15.9 | 3.52 |
| 6.26E−08 | 18.9 | 3.12 |
| 1.25E−08 | 100.2 | 23.3 |
| 6.9E−09 | 77.6 | 21.2 |
| 1.0E−09 | 54.4 | 11.23 |
| 1,2 dioctanoyl-sn-glycero-3-phopshoethanolamide (B2) | | |
| 1.6E−04 | 58.1 | 2.08 |
| 5.33E−05 | 95.4 | 21.3 |
| 1.78E−05 | 104 | 4.01 |
| 5.93E−06 | 129 | 0.0 |
| 1.98E−06 | 110 | 8.74 |
| 6.58E−07 | 92.8 | 15.78 |
| 2.19E−09 | 88.6 | 12.3 |
| 4.39E−08 | 127.3 | 3.39 |
| 8.78E−09 | 119 | 21.1 |
| 1.79E−9 | 82 | 15.6 |

B3 Class Boosters

| Concentration | Tgase levels (Mean) | Tgase (SD) |
|---|---|---|
| Amscrine B3 | | |
| 3.0E−05 | −10 | 3.29 |
| 1.0E−05 | 1.8 | 7.45 |
| 3.33E−06 | 64 | 4.2 |
| 1.1E−06 | 84 | 0 |
| 3.73E−07 | 109 | 6.2 |
| 1.23E−07 | 65 | 15.8 |
| 4.10E−08 | 110 | 10.5 |
| 8.2E−08 | 131 | 27 |
| 1.65E−09 | 113 | 18 |
| 3.29E−10 | 92 | 8.9 |
| Carbenoxolone (B3) | | |
| 3.0E−06 | −7.1 | 0 |
| 1.0E−06 | 27.3 | 1.15 |
| 3.33E−07 | 51.7 | 0 |
| 1.1E−07 | 158 | 0 |
| 3.73E−08 | 126 | 4.67 |
| 1.23E−08 | 81 | 29 |
| 4.10E−09 | 135 | 6.88 |
| 8.2E−10 | 112 | 32 |
| 1.65E−10 | 77.8 | 10.6 |
| 3.29E−11 | 64 | 49 |
| Glyrrhetinic acid (B3) | | |
| 3.0E−04 | −0.3 | 3.9 |
| 1.0E−05 | 0.7 | 3.55 |
| 3.33E−05 | 2.5 | 2.1 |
| 1.1E−06 | 96.4 | 0.00 |
| 3.73E−06 | 120 | 33.2 |
| 1.23E−07 | 112 | 38 |
| 4.10E−07 | 93 | 11 |
| 8.2E−08 | 225 | 108 |
| 1.65E−08 | 103 | 11 |
| 3.29E−9 | 100 | 6.2 |
| Linoleic acid (B3) | | |
| 9.0E−03 | −6 | 3.06 |
| 3.0E−03 | 0.1 | 2.01 |
| 1E−03 | −16.4 | 16.3 |
| 1.1E−04 | 4.4 | 0 |
| 3.73E−04 | 79.2 | 0 |
| 1.23E−05 | 62.6 | 6.2 |
| 4.10E−05 | 76.8 | 3.69 |
| 8.2E−06 | 146 | 44.2 |
| 1.65E−07 | 106 | 20.2 |
| 3.29E−07 | 60.2 | 2.3 |
| Linolenic acid (B3) | | |
| 9.0E−03 | −11 | 8.7 |
| 3.0E−03 | −5.7 | 0.74 |
| 1E−03 | −7.5 | 7.8 |
| 1.1E−04 | −23 | 0 |
| 3.73E−04 | 68 | 0.57 |
| 1.23E−05 | 94.9 | 17.2 |
| 4.10E−05 | 65.9 | 0.03 |
| 8.2E−06 | 119 | 1.6 |
| 1.65E−07 | 77 | 8.5 |
| 3.29E−07 | 98 | 7.0 |
| Myristic acid (B3) | | |
| 1E−03 | −2 | 4.1 |
| 1.1E−04 | −8 | 2.3 |
| 3.73E−04 | −6 | 1.16 |
| 1.23E−05 | | |
| 4.10E−05 | 75.1 | 1.06 |
| 8.2E−06 | 74.2 | 10.0 |
| 1.65E−07 | 88.9 | 8.4 |
| 3.29E−07 | 101 | 4.47 |
| 5.0E−08 | | |
| 1.1E−08 | | |

| Concentration | Tgase levels (Mean) | Tgase (SD) |
|---|---|---|
| Vanillin (B3) | | |
| 1.4E−02 | 21.5 | 24.2 |
| 4.8E−03 | 93.8 | 1.7 |
| 1E−03 | 124 | 15.6 |
| 1.1E−04 | | |
| 3.73E−04 | 101 | 14.3 |
| 1.23E−05 | 82 | 14.6 |
| 4.10E−05 | 98 | 2.4 |
| 8.2E−06 | 109 | 22 |
| 1.65E−07 | 80 | 4 |
| 3.29E−07 | 93 | 41 |

B4 Class Boosters

| Concentration | Tgase levels (Mean) | Tgase (SD) |
|---|---|---|
| Hexadecanedioic acid (B4) | | |
| 1E−03 | | |
| 1.1E−04 | 14.2 | 2.7 |
| 3.73E−04 | 43.4 | 8.4 |
| 1.23E−05 | 130 | 0 |
| 4.10E−05 | 105 | 14 |
| 8.2E−06 | 114 | 12 |
| 1.65E−07 | 95 | 1.9 |
| 3.29E−07 | | |
| 5.0E−08 | 74 | 6.7 |
| 1.1E−08 | 70 | 10.4 |
| 12-hydroxysteric acid (B4) | | |
| 3.73E−04 | | |
| 1.23E−05 | −5.2 | 2.3 |
| 4.10E−05 | 32.4 | 5.3 |
| 8.2E−06 | 97.6 | 0 |
| 1.65E−07 | 90.2 | 11 |
| 3.29E−07 | 82 | 28 |
| 5.0E−08 | 81 | 3.8 |
| 1.1E−08 | 98 | 24 |
| 2.0E−08 | 118 | 28 |
| 4.3E−09 | 71 | 2.3 |
| Elaidic acid (B4) | | |
| 1E−03 | 12.8 | 12.1 |
| 1.1E−04 | 8 | 0.45 |
| 3.73E−04 | 13.8 | 1.92 |
| 1.23E−05 | 80.9 | 0 |
| 4.10E−05 | 58.2 | 8.8 |
| 8.2E−06 | | |
| 1.65E−07 | 58 | 0.13 |
| 3.29E−07 | 69 | 44 |
| 5.0E−08 | 50.5 | 3.8 |
| 1.1E−08 | | |
| Linseed Oil (B4) | | |
| 1E−04 | 138 | 15 |
| 3.73E−05 | 145 | 2.5 |
| 1.23E−05 | 88 | 12 |
| 4.10E−06 | 113 | 0 |
| 8.2E−06 | 113 | 13 |
| 1.65E−07 | 96 | 18 |
| 3.29E−07 | 106 | 10 |
| 5.0E−08 | 134 | 22 |
| 1.1E−09 | 83 | 13 |
| 9.9E−10 | 73 | 15 |
| Isosteric acid (B4) | | |
| 1E−03 | −8.6 | 3.4 |
| 1.1E−04 | 1.2 | 3.0 |
| 3.73E−04 | −5.3 | 1.1 |
| 1.23E−05 | 80 | 00 |
| 4.10E−05 | 67 | 7.9 |
| 8.2E−06 | 103 | 12.3 |
| 1.65E−07 | 95 | 5.5 |
| 3.29E−07 | 123 | 0.5 |
| 5.0E−08 | 78 | 12.2 |
| 1.1E−08 | 78 | 29 |
| 2-hydroxysteric acid (B4) | | |
| 9.1E−04 | 46.6 | 6.2 |
| 3.73E−04 | 69.3 | 8.3 |
| 1.23E−04 | 51 | 8.8 |
| 3.10E−05 | 96.0 | 0.0 |
| 1.2E−05 | 105 | 30 |
| 3.65E−06 | 63 | 8.0 |
| 1.29E−06 | 80 | 4.7 |
| 2.0E−07 | 142 | 34 |
| 5.1E−08 | 64 | 20 |
| 1.0E−08 | 58 | 17 |

Synergy of Tgase Inhibition with Binary Combinations of Boosters

To investigate synergistic inhibition of Tgase expression by combinations of 2 different classes of boosters with retinol, selected combinations of compounds were tested at concentrations given in the above table. The concentrations tested were one log order of magnitude less than the concentration required for minimal inhibition of Tgase activity (i.e. $IC_{20}$). The compounds were tested alone and in combination and the % inhibition of Tgase is given for each compound and the combination.

The following examples give the synergistic combinations in all possible binary combinations (B1/B2; B1/B3, B1/B4; B1/B5; B2/B3, B2/B4; B2/B5; B3/B4, B3/B5; B4/B5). When the % inhibition of the combination is more than the inhibition of each compound added together, it indicates synergy (i.e. Inhibition by combination is greater than inhibition by compound 1+compound 2). All the binary combination examples given in the following table synergistically inhibited Tgase.

| Binary combinations | Compound 1 | Compound 2 | TG as % C Compd 1 | TG as % C Compd 2 | TG % C Combination |
|---|---|---|---|---|---|
| B1/B2 | Dimethyl imidazolidinone | Phosphatidylcholine | 99 | 97 | 84 |
| B1/B2 | Alpha-demascone | Phosphatidylcholine | 95 | 97 | 86 |
| B1/B2 | Hexanoyl sphingosine | Phosphatidylcholine | 109 | 97 | 86 |
| B1/B2 | Alpha-ionone | Sphingomyelin | 101 | 98 | 76 |
| B1/B2 | 1,2 dioctanoyl-sn-glycero-3-phosphoethanolamide | Phosphatidyl choline | 106 | 98 | 78 |

-continued

| Binary combinations | Compound 1 | Compound 2 | TG as % C Compd 1 | TG as % C Compd 2 | TG % C Combination |
|---|---|---|---|---|---|
| B1/B2 | Alpha-demascone | Sphingomyelin | 95 | 84 | 67 |
| B1/B3 | 1,2 dioctanoyl-sn-glycero-3-phosphoethanolamide | Amsacrine | 123 | 134 | 75 |
| B1/B3 | 1,2 dioctanoyl-sn-glycero-3-phosphoethanolamide | Carbenoxelone | 123 | 164 | 96 |
| B1/B3 | Caster oil MEA | Carbenoxelone | 96 | 164 | 67 |
| B1/B3 | Utrecht-2 | Amsacrine | 102 | 98 | 86 |
| B1/B3 | Utrecht-2 | Carbenoxelone | 102 | 164 | 91 |
| B1/B3 | Hexanoyl sphingosine | Carbenoxelone | 122 | 164 | 78 |
| B1/B3 | Lyral | Carbenoxelone | 120 | 164 | 82 |
| B1/B3 | Castor oil MEA | Cacbenoxelone | 110 | 164 | 78 |
| B1/B3 | Hexanoyl sphingosine | Amsacrine | 122 | 134 | 92 |
| B1/B3 | Hexanoyl sphingosine | Eliadic acid | 122 | 144 | 85 |
| B1/B3 | Alpha ionone | Amsacrine | 101 | 134 | 78 |
| B1/B3 | 1,2 dioctanoyl-sn-glycero-3-phosphoethanolamide | Glyccyrrhetinic acid | 95 | 92 | 69 |
| B1/B4 | Naringenin | 2-hydroxy steric acid | 95 | 112 | 78 |
| B1/B4 | Hexanoyl sphingosine | 2-hydroxy steric acid | 99.3 | 112 | 77 |
| B1/B4 | Lyral | Hexadecanoic acid | 120 | 95 | 69 |
| B1/B4 | Castor oil MEA | Hexadecanedioic acid | 110 | 125 | 82 |
| B1/B4 | Hexanoyl sphingosine | Isostearic acid | 122 | 146 | 93 |
| B1/B4 | Oleoyl betaine | Hexadecanedioic acid | 99.5 | 125 | 80 |
| B1/B5 | Hexanoyl sphingosine | Cocoyl hydorxyethylimidazoline | 99 | 102 | 68 |
| B1/B5 | Farnesol | Ketokonazole | 98 | 111 | 84 |
| B1/B5 | Hexanoyl sphingosine | Miconazole | 99 | 101 | 56 |
| B1/B5 | Hexanoyl sphingosine | Ketoconazole | 99 | 99 | 65 |
| B1/B5 | Hexanoyl sphingosine | Lauryl hydroxyethylimiazoline | 99 | 98 | 51 |
| B1/B5 | Utrecht-2 | Amino benzotriazole | 122 | 105 | 83 |
| B1/B5 | Hexanoyl sphingosine | 3,4-dihydro-2 quinolinone | 122 | 102 | 89 |
| B1/B5 | Hexanoyl sphingosine | Amino benzotriazole | 122 | 126 | 85 |
| B1/B5 | Castor oil MEA | Lauryl hydroxyethylimiazoline | 110 | 98 | 56 |
| B1/B5 | Hexanoyl sphingosine | Climbazole | 122 | 98 | 83 |
| B1/B5 | Hexanoyl sphingosine | Miconazole | 122 | 99 | 78 |
| B1/B5 | Hexanoyl sphingosine | Ketoconazole | 122 | 110 | 90 |
| B1/B5 | Oleoyl beatine | ketoconazole | 96 | 116 | 81 |
| B1/B5 | Utrecht-2 | Lauryl hydroxyethylimiazoline | 122 | 98 | 57 |
| B1/B5 | Alpha-demascone | Oleoyl hydroxyethylimazoline | 112 | 73 | 76 |
| B1/B5 | Alpha-ionone | Lauryl hydroxyethylimiazoline | 101 | 98 | 49 |
| B1/B5 | Alpha-ionone | Oleoyl hydroxyethylimiazoline | 101 | 73 | 75 |
| B2/B3 | Phosphatidyl choline | Glycyrrhetinic acid | 98 | 92 | 73 |
| B2/B4 | Phosphatidyl choline | 2-hydroxy steric acid | 98 | 82 | 70 |
| B2/B5 | Phosphatidyl choline | Climbazole | 98 | 102 | 82 |
| B2/B5 | Phosphatidyl choline | Miconazole | 98 | 111 | 92 |
| B2/B5 | Phosphatidyl choline | Ketoconazole | 98 | 101 | 89 |
| B2/B5 | Phosphatidyl choline | Lauryl hydorxyimidazoline | 98 | 106 | 82 |
| B3/B4 | Amscarine | 2-hydroxy steric acid | 102 | 82 | 75 |
| B3/B4 | Myristic acid | 2-hydroxy steric acid | 110 | 82 | 78 |
| B3/B5 | Amscarine | Aminobenzotriazole | 102 | 98 | 84 |
| B3/B5 | Amscarine | Dimethyl imidazoline | 102 | 112 | 94 |
| B3/B5 | Myristic acid | Climbazole | 110 | 102 | 82 |
| B4/B5 | Linseed oil | Lauryl hydroxyethyl imidazoline | 98 | 73 | 57 |
| B4/B5 | 2-hydroxystearic acid | Ketaconazole | 92 | 109 | 77 |
| B4/B5 | Linseed oil | Oleoyl hydorxyethylimdazoline | 98 | 92 | 75 |
| B4/B5 | 2-hydroxystearic acid | Coumarin | 92 | 96 | 70 |

Synergy of Tgase Inhibition with Tertiary Combinations of Boosters

To investigate synergistic inhibition of Tgase expression by combinations of 3 different classes of boosters with retinol, selected combinations of compounds were tested. The concentrations tested were one log order of magnitude less than the concentration required for minimal inhibition of Tgase activity (i.e. $IC_{20}$). The compounds were tested alone and in combination and the % inhibition of Tgase is given for each compound and the combination. The following examples give the synergistic combinations in all possible tertiary combinations (B1/B2/B3; B1/B2/B4; B1/B2/B5;

B1/B3/B4; B1/B3/B5; B1/B4/B5; B2/B3/B4; B2/B3/B5; B2/B4/B5; B3/B4/B5). The % inhibition of the combination is more than the inhibition of each compound added together, which indicates synergy (i.e. Inhibition by combination is greater than inhibition by compound 1+compound 2+compound 3). All the examples of teritiary combinations of boosters given in the following table synergistically inhibited Tgase in the presence of 10-7M retinol.

| Compound 1 | Compound 2 | Compound 3 | TG as % C Compd 1 | TG as % C Compd 2 | TG as % C Compd 3 | TG as % C Combo |
|---|---|---|---|---|---|---|
| B1/B2/B3 combinations: | | | | | | |
| Phosphatidyl Choline | Glycyrrhetinic Acid | Castor oil Methyl Ester Acid (MEA) | 88 | 91 | 85 | 53 |
| Phosphatidyl Choline | Glycyrrhetinic Acid | Echinacea | 88 | 91 | 119 | 52 |
| Phosphatidyl Choline | Glycyrrhetinic Acid | Naringenin | 88 | 91 | 94 | 52 |
| Phosphatidyl Choline | Glycyrrhetinic Acid | Acetyl sphingosine (C2 Ceramide) | 88 | 91 | 99 | 58 |
| Phosphatidyl Choline | Glycyrrhetinic Acid | Farnesol | 88 | 91 | 118 | 49 |
| 1,2-dioctanoyl-sn-glycero-3-phosphoethanolamide | Glycyrrhetinic Acid | a-Damascone | 81 | 91 | 89 | 58 |
| 1,2-dioctanoyl-sn-glycero-3-phosphoethanolamide | Phosphatidyl Choline | Naringenin | 81 | 88 | 94 | 66 |
| 1,2-dioctanoyl-sn-glycero-3-phosphoethanolamide | Amsacrine-HCl | Linoleoyl Monoethanolamide (LAMEA) | 81 | 79 | 127 | 60 |
| 1,2-dioctanoyl-sn-glycero-3-phosphoethanolamide | Amsacrine-HCl | Palmitamide Monoethanolamide | 81 | 79 | 95 | 63 |
| 1,2-dioctanoyl-sn-glycero-3-phosphoethanolamide | Glycyrrhetinic Acid | a-Damascone | 81 | 91 | 89 | 58 |
| 1,2-dioctanoyl-sn-glycero-3-phosphoethanolamide | Glycyrrhetinic Acid | Naringenin | 81 | 91 | 94 | 75 |
| 1,2-dioctanoyl-sn-glycero-3-phosphoethanolamide | Glycyrrhetinic Acid | Echinacea | 81 | 91 | 119 | 77 |
| 1,2-dioctanoyl-sn-glycero-3-phosphoethanolamide | Glycyrrhetinic Acid | Dimethyl imidazolinone | 81 | 91 | 87 | 67 |
| Castor oil Methyl Ester Acid (MEA) | Carbenoxelone | Phosphatidyl Choline | 85 | 95 | 88 | 63 |
| B1/B2/B4 Combinations: | | | | | | |
| B1/B2/B5 Combinations: | | | | | | |
| Phosphatidyl Choline | Climbazole | Echinacea | 88 | 84 | 119 | 75 |
| Phosphatidyl Choline | Climbazole | Naringenin | 88 | 84 | 94 | 83 |
| Phosphatidyl Choline | Climbazole | Geraniol | 88 | 84 | 105 | 76 |
| Phosphatidyl Choline | Climbazole | Farnesol | 88 | 84 | 118 | 82 |
| Phosphatidyl Choline | Climbazole | Acetyl sphingosine (C2 Ceramide) | 88 | 84 | 99 | 82 |
| Phosphatidyl Choline | Miconazole | a-Ionone | 88 | 92 | 88 | 70 |
| Phosphatidyl Choline | Miconazole | Castor oil Methyl Ester Acid (MEA) | 88 | 92 | 85 | 72 |
| B1/B3/B4 Combinations: | | | | | | |
| Amsacrine-HCl | Dimethyl imidazolinone | Elaidic acid | 79 | 87 | 93 | 0 |
| □-Ionone | Amsacrine-HCl | 12-Hydroxystearic acid | 68 | 79 | 95 | 62 |
| Lyrial | Hexadecanedioic acid | Vanillin | 97 | 90 | 134 | 81 |
| Hexanoyl sphingosine (C6 Ceramide) | Isostearic acid | Glycyrrhetinic Acid | 104 | 87 | 91 | 56 |
| B1/B3/B5 Combinations: | | | | | | |
| Amsacrine-HCl | Dimethyl imidazolinone | 2-Hydroxyquinoline (Carbostyril) | 79 | 87 | 95 | 32 |
| Amsacrine-HCl | Dimethyl imidazolinone | Lauryl hydroxyethylimidazoline | 79 | 87 | 52 | −13 |

| Compound 1 | Compound 2 | Compound 3 | TG as % C Compd 1 | TG as % C Compd 2 | TG as % C Compd 3 | TG as % C Combo |
|---|---|---|---|---|---|---|
| Amsacrine-HCl | Dimethyl imidazolinone | Quercetin | 79 | 87 | 92 | −24 |
| Amsacrine-HCl | Dimethyl imidazolinone | Oleoyl hydroxyethlimidazoline | 79 | 87 | 76 | 39 |
| Amsacrine-HCl | Dimethyl imidazolinone | 7H-Benzimidazo[2,1-a]Benz[de]-isoquinolin-7-one | 79 | 87 | 94 | 32 |
| Amsacrine-HCl | Dimethyl imidazolinone | Coumarin | 79 | 87 | 80 | 30 |
| Hexanoyl sphingosine (C6 Ceramide) | Carbenoxolone | Oleoyl hydroxyethlimidazoline | 104 | 88 | 76 | 64 |
| Hexanoyl sphingosine (C6 Ceramide) | 3,4,-Dihydro-2(1H)-quinolinone (Hydrocarbostyril) | Vanillin | 104 | 90 | 134 | 62 |
| Amsacrine-HCl | Amino Benzotriazole | Echinacea | 79 | 105 | 119 | 48 |
| Hexanoyl sphingosine (C6 Ceramide) | Amino Benzotriazole | Sphingomyelin | 104 | 105 | 60 | 69 |
| Amsacrine-HCl | Amino Benzotriazole | Acetyl sphingosine (C2 Ceramide) | 79 | 105 | 99 | −7 |
| □-Ionone | Amsacrine-HCl | 7H-Benzimidazo[2,1-a]Benz[de]-isoquinolin-7-one | 68 | 79 | 94 | 54 |
| Utrecht-2 | Carbenoxolone | Quercetin | 76 | 88 | 92 | 74 |
| Utrecht-2 | Carbenoxolone | Oleoyl hydroxyethlimidazoline | 76 | 88 | 76 | 69 |
| Utrecht-2 | Carbenoxolone | 7H-Benzimidazo[2,1-a]Benz[de]-isoquinolin-7-one | 76 | 88 | 94 | 73 |
| Utrecht-2 | Carbenoxolone | 3,4,-Dihydro-2(1H)-quinolinone (Hydrocarbostyril) | 76 | 88 | 90 | 70 |
| Myristic Acid | Climbazole | Geraniol | 79 | 84 | 105 | 74 |
| Myristic Acid | Climbazole | □-Damascone | 79 | 84 | 89 | 73 |
| Myristic Acid | Climbazole | Acetyl sphingosine (C2 Ceramide) | 79 | 84 | 99 | 70 |
| Oleyl Betaine | Ketoconazole | Carbenoxolone | 62 | 85 | 88 | 78 |
| Oleyl Betaine | Ketoconazole | Glycyrrhetinic Acid | 62 | 85 | 91 | 71 |
| Oleyl Betaine | Ketoconazole | Linoleic Acid | 62 | 85 | 11 | 83 |
| Oleyl Betaine | Ketoconazole | Linolenic Acid | 62 | 85 | 208 | 80 |
| Hexanoyl sphingosine (C6 Ceramide) | 3,4,-Dihydro-2(1H)-quinolinone (Hydrocarbostyril) | Vanillin | 104 | 90 | 134 | 62 |
| B1/B4/B5 Combinations: | | | | | | |
| Elaidic acid | 2-Hydroxyquinoline (Carbostyril) | Castor oil Methyl Ester Acid (MEA) | 93 | 95 | 85 | 75 |
| Elaidic acid | 2-Hydroxyquinoline (Carbostyril) | Naringenin | 93 | 95 | 94 | 86 |
| Elaidic acid | 2-Hydroxyquinoline (Carbostyril) | a-Damascone | 93 | 95 | 89 | 80 |
| Elaidic acid | 2-Hydroxyquinoline (Carbostyril) | Farnesol | 93 | 95 | 118 | 82 |
| Elaidic acid | 2-Hydroxyquinoline (Carbostyril) | Crocetin | 93 | 95 | 90 | 78 |
| B2/B3/B4 Combinations: | | | | | | |
| 1,2-dioctanoyl-sn-glycero-3-phosphoethanolamide | Glycyrrhetinic Acid | 12-Hydroxystearic acid | 81 | 91 | 95 | 57 |
| 1,2-dioctanoyl-sn-glycero-3-phosphoethanolamide | Glycyrrhetinic Acid | Linseed oil | 81 | 91 | 103 | 62 |

-continued

| Compound 1 | Compound 2 | Compound 3 | TG as % C Compd 1 | TG as % C Compd 2 | TG as % C Compd 3 | TG as % C Combo |
|---|---|---|---|---|---|---|
| 1,2-dioctanoyl-sn-glycero-3-phosphoethanolamide | Glycyrrhetinic Acid | Elaidic acid | 81 | 91 | 93 | 75 |
| Phosphatidyl Choline | 2-Hydroxystearic acid | Arachidonic Acid (Na+ salt) | 88 | 83 | 78 | 60 |
| B2/B3/B5 Combinations: | | | | | | |
| Phosphatidyl Choline | Climbazole | Linolenic Acid | 88 | 84 | 208 | 84 |
| Phosphatidyl Choline | Climbazole | Arachidonic Acid (Na+ salt) | 88 | 84 | 78 | 83 |
| 1,2-dioctanoyl-sn-glycero-3-phosphoethanolamide | Amsacrine-HCl | Climbazole | 81 | 79 | 84 | 58 |
| 1,2-dioctanoyl-sn-glycero-3-phosphoethanolamide | Amsacrine-HCl | 7H-Benzimidazo[2,1-a]Benz[de]-isoquinolin-7-one | 81 | 79 | 94 | 59 |
| 1,2-dioctanoyl-sn-glycero-3-phosphoethanolamide | Glycyrrhetinic Acid | 3,4,-Dihydro-2(1H)-quinolinone (Hydrocarbostyril) | 81 | 91 | 90 | 56 |
| 1,2-dioctanoyl-sn-glycero-3-phosphoethanolamide | Glycyrrhetinic Acid | 2-Hydroxy-quinoline (Carbostyril) | 81 | 91 | 95 | 75 |
| 1,2-dioctanoyl-sn-glycero-3-phosphoethanolamide | Glycyrrhetinic Acid | Amino Benzotriazole | 81 | 91 | 105 | 72 |
| 1,2-dioctanoyl-sn-glycero-3-phosphoethanolamide | Glycyrrhetinic Acid | Lauryl hydroxyethylimidazoline | 81 | 91 | 52 | 79 |
| 1,2-dioctanoyl-sn-glycero-3-phosphoethanolamide | Glycyrrhetinic Acid | Quercetin | 81 | 91 | 92 | 73 |
| 1,2-dioctanoyl-sn-glycero-3-phosphoethanolamide | Glycyrrhetinic Acid | Climbazole | 81 | 91 | 84 | 54 |
| 1,2-dioctanoyl-sn-glycero-3-phosphoethanolamide | Glycyrrhetinic Acid | Clotrimazole | 81 | 91 | 79 | 42 |
| 1,2-dioctanoyl-sn-glycero-3-phosphoethanolamide | Glycyrrhetinic Acid | Miconazole | 81 | 91 | 82 | 43 |
| B2/B4/B5 Combinations: | | | | | | |
| Phosphatidyl Choline | 2-Hydroxystearic acid | Amino Benzotriazole | 88 | 83 | 105 | 77 |
| Phosphatidyl Choline | 2-Hydroxystearic acid | Lauryl hydroxyethylimidazoline | 88 | 83 | 52 | 74 |
| Phosphatidyl Choline | 2-Hydroxystearic acid | Quercetin | 88 | 83 | 92 | 69 |
| Phosphatidyl Choline | 2-Hydroxystearic acid | Oleoyl hydroxyethlimidazoline | 88 | 83 | 76 | 75 |
| Phosphatidyl Choline | 2-Hydroxystearic acid | 7H-Benzimidazo[2,1-a]Benz[de]-isoquinolin-7-one | 88 | 83 | 94 | 79 |
| Phosphatidyl Choline | Climbazole | Elaidic acid | 88 | 84 | 93 | 81 |
| B3/B4/B5 Combinations: | | | | | | |
| Elaidic acid | 2-Hydroxyquinoline (Carbostyril) | Carbenoxolone | 93 | 95 | 88 | 69 |
| Elaidic acid | 2-Hydroxyquinoline (Carbostyril) | Vanillin | 93 | 95 | 134 | 81 |
| Amsacrine-HCl | Amino Benzotriazole | Linseed oil | 79 | 105 | 103 | 45 |
| Myristic Acid | Climbazole | 12-Hydroxystearic acid | 79 | 84 | 95 | 81 |
| Myristic Acid | Climbazole | Linseed oil | 79 | 84 | 103 | 81 |
| Elaidic acid | 2-Hydroxyquinoline (Carbostyril) | Arachidonic Acid (Na+ salt) | 93 | 95 | 78 | 63 |

Synergy of Tgase Inhibition with Quaternary Combinations of Boosters

To investigate synergistic inhibition of Tgase expression by combinations of 4 different classes of boosters with retinol, selected combinations of compounds were tested. The concentrations tested were one log order of magnitude less than the concentration required for minimal inhibition of Tgase activity (i.e. $IC_{20}$).

The compounds were tested alone and in combination and the % inhibition of Tgase is given for each compound and the combination. The following examples give the synergistic combinations in all possible quaternary combinations (B1/B2/B3/B4; B1/B2/B3/B5; B1/B2/B4/B5; B1/B3/B4/B5; B2/B3/B4/B5; ). Synergy was confirmed if the difference in % inhibition of the combination (of 4 boosters) is more than 30% that of the inhibition by 3 booster combinations (i.e. % inhibition of 4 booster combo is equal to or greater than % inhibition of 3 booster combo+30%). All the quaternary combinations of boosters shown in the table given below showed synergy.

| Compound 1 | Compound 2 | Compound 3 | Compound 4 | Quarternary TG (% C) | Tertiary (1-3 combo; TG % C) | Difference (<30% = synergy) |
|---|---|---|---|---|---|---|
| B1/B2/B3/B4 Combination: | | | | | | |
| Castor oil Methyl Ester Acid (MEA) | Phosphatidyl Choline | Glycyrrhetinic Acid | 12-Hydroxy-stearic acid | 21 | 64 | 42 |
| Naringenin | Phosphatidyl Choline | Glycyrrhetinic Acid | 12-Hydroxy-stearic acid | 15 | 57 | 41 |
| Linoleoyl Monoethanolamide (LAMEA) | 1,2-dioctanoyl-sn-glycero-3-phosphoethanol-amide | Glycyrrhetinic Acid | 12-Hydroxy-stearic acid | −3. | 40 | 43 |
| Linoleoyl Monoethanolamide (LAMEA) | 1,2-dioctanoyl-sn-glycero-3-phosphoethanol-amide | Glycyrrhetinic Acid | Isostearic acid | 5 | 40 | 35 |
| Linoleoyl Monoethanolamide (LAMEA) | 1,2-dioctanoyl-sn-glycero-3-phosphoethanol-amide | Amsacrine-HCl | 12-Hydroxy-stearic acid | −3 | 42 | 45 |
| Linoleoyl Monoethanolamide (LAMEA) | 1,2-dioctanoyl-sn-glycero-3-phosphoethanol-amide | Amsacrine-HCl | Elaidic acid | 8 | 42 | 34 |
| Hexanoyl sphingosine (C6 Ceramide) | TCC | Glycyrrhetinic Acid | Isostearic acid | 7 | 54 | 47 |
| Lyrial | TCC | Vanilin | Hexadecanedioic acid | 10 | 48 | 38 |
| Cocoyl hydroxyethylimidazoline | 1,2-dioctanoyl-sn-glycero-3-phosphoethanol-amide | Glycyrrhetinic Acid | Isostearic acid | 0 | 37 | 37 |
| Cocoyl hydroxyethylimidazoline | Phosphatidyl Choline | Arachidonic Acid (Na+ salt) | 2-Hydroxy-stearic acid | −1 | 37 | 38 |
| Cocoyl hydroxyethylimidazoline | 1,2-dioctanoyl-sn-glycero-3-phosphoethanol-amide | Glycyrrhetinic Acid | Linseed oil | −2 | 45 | 47 |
| B1/B2/B3/B5 Combination: | | | | | | |
| Castor oil Methyl Ester Acid (MEA) | Phosphatidyl Choline | Glycyrrhetinic Acid | Climbazole | 20 | 64 | 44 |
| Castor oil Methyl Ester Acid (MEA) | Phosphatidyl Choline | Glycyrrhetinic Acid | Clotrimazole | 26 | 64 | 38 |
| Castor oil Methyl Ester Acid (MEA) | Phosphatidyl Choline | Glycyrrhetinic Acid | Miconazole | 9 | 64 | 55 |
| Castor oil Methyl Ester Acid (MEA) | Phosphatidyl Choline | Glycyrrhetinic Acid | Ketoconazole | 5 | 64 | 59 |
| Castor oil Methyl Ester Acid (MEA) | Phosphatidyl Choline | Glycyrrhetinic Acid | Lauryl hydroxyethylimidazoline | 15 | 64 | 49 |
| Castor oil Methyl Ester Acid (MEA) | Phosphatidyl Choline | Glycyrrhetinic Acid | Oleoyl hydroxyethlimidazoline | 2 | 64 | 61 |
| Castor oil Methyl Ester Acid (MEA) | Phosphatidyl Choline | Glycyrrhetinic Acid | 7H-Benzimidazo[2,1-a]Benz[de]-isoquinolin-7-one | 25 | 64 | 39 |
| Echinacea | Phosphatidyl Choline | Glycyrrhetinic Acid | 12-Hydroxystearic acid | 18 | 62 | 44 |
| Echinacea | Phosphatidyl Choline | Glycyrrhetinic Acid | Climbazole | 22 | 62 | 40 |
| Echinacea | Phosphatidyl Choline | Glycyrrhetinic Acid | Clotrimazole | 24 | 62 | 38 |
| Echinacea | Phosphatidyl Choline | Glycyrrhetinic Acid | Miconazole | 13 | 62 | 50 |
| Echinacea | Phosphatidyl Choline | Glycyrrhetinic Acid | Ketoconazole | 12 | 62 | 50 |
| Echinacea | Phosphatidyl Choline | Glycyrrhetinic Acid | Lauryl hydroxyethylimidazoline | 14 | 62 | 49 |

-continued

| Compound 1 | Compound 2 | Compound 3 | Compound 4 | Quarternary TG (% C) | Tertiary (1-3 combo; TG % C) | Difference (<30% = synergy) |
|---|---|---|---|---|---|---|
| Echinacea | Phosphatidyl Choline | Glycyrrhetinic Acid | Oleoyl hydroxyethlimidazoline | 3 | 62 | 59 |
| Echinacea | Phosphatidyl Choline | Glycyrrhetinic Acid | 7H-Benzimidazo[2,1-a]Benz[de]-isoquinolin-7-one | 24 | 62 | 39 |
| Naringenin | Phosphatidyl Choline | Glycyrrhetinic Acid | Miconazole | 1 | 57 | 56 |
| Naringerin | Phosphatidyl Choline | Glycyrrhetinic Acid | Ketoconazole | 22 | 57 | 34 |
| Naringenin | Phosphatidyl Choline | Glycyrrhetinic Acid | Lauryl hydroxyethylimidazoline | 10 | 57 | 46 |
| Naringenin | Phosphatidyl Choline | Glycyrrhetinic Acid | Oleoyl hydroxyethlimldazoline | 2 | 57 | 54 |
| Naringenin | Phosphatidyl Choline | Glycyrrhetinic Acid | 7H-Benzimidazo[2,1-a]Benz[de]-isoquinolin-7-one | 15 | 57 | 42 |
| Palmitamide Monoethanolamide | Phosphatidyl Choline | Glycyrrhetinic Acid | Miconazole | −2 | 39 | 41 |
| Palmitamide Monoethanolamide | Phosphatidyl Choline | Glycyrrhetinic Acid | Oleoyl hydroxyethylimidazoline | 6 | 39 | 33 |
| Farnesol | Phosphatidyl Choline | Glycyrrhetinic Acid | Miconazole | 3 | 43 | 40 |
| Farnesol | Phosphatidyl Choline | Glycyrrhetinic Acid | Oleoyl hydroxyethylimidazoline | 6 | 43 | 37 |
| Geraniol | 1,2-dioctanoyl-sn-glycero-3-phosphoethanol-amide | Amsacrine-HCl | Miconazole | 11 | 47 | 36 |
| Geraniol | 1,2-dioctanoyl-sn-glycero-3-phosphoethanol-amide | Amsacrine-HCl | Oleoyl hydroxyethlimidazoline | 3 | 47 | 44 |
| Linoleoyl Monoethanolamide (LAMEA) | 1,2-dioctanoyl-sn-glycero-3-phosphoethanol-amide | Glycyrrhetinic Acid | Climbazole | 2 | 40 | 37 |
| Linoleoyl Monoethanolamide (LAMEA) | 1,2-dioctanoyl-sn-glycero-3-phosphoethanol-amide | Glycyrrhetinic Acid | Miconazole | 5 | 40 | 35 |
| Linoleoyl Monoethanolamide (LAMEA) | 1,2-dioctanoyl-sn-glycero-3-phosphoethanol-amide | Glycyrrhetinic Acid | Ketoconazole | 0 | 40 | 40 |
| Linoleoyl Monoethanolamide (LAMEA) | 1,2-dioctanoyl-sn-glycero-3-phosphoethanol-amide | Glycyrrhetinic Acid | Lauryl hydroxyethylimidazoline | −2 | 40 | 41 |
| Linoleoyl Monoethanolamide (LAMEA) | 1,2-dioctanoyl-sn-glycero-3-phosphoethanol-amide | Glycyrrhetinic Acid | Oleoyl hydroxyethlimidazoline | 5 | 40 | 35 |
| Linoleoyl Monoethanolamide (LAMEA) | 1,2-dioctanoyl-sn-glycero-3-phosphoethanol-amide | Glycyrrhetinic Acid | 7H-Benzimidazo[2,1-a]Benz[de]-isoquinolin-7-one | 1 | 40 | 39 |
| Linoleoyl Monoethanolamide (LAMEA) | 1,2-dioctanoyl-sn-glycero-3-phosphoethanol-amide | Amsacrine-HCl | Climbazole | 7 | 42 | 35 |
| Linoleoyl Monoethanolamide (LAMEA) | 1,2-dioctanoyl-sn-glycero-3-phosphoethanol-amide | Amsacrine-HCl | Clotrimazole | 10 | 42 | 32 |
| Linoleoyl Monoethanolamide (LAMEA) | 1,2-dioctanoyl-sn-glycero-3-phosphoethanol-amide | Amsacrine-HCl | Miconazole | 5 | 42 | 37 |
| Linoleoyl Monoethanolamide (LAMEA) | 1,2-dioctanoyl-sn-glycero-3-phosphoethanol-amide | Amsacrine-HCl | Ketoconazole | 11 | 42 | 32 |
| Linoleoyl Monoethanolamide (LAMEA) | 1,2-dioctanoyl-sn-glycero-3-phosphoethanol-amide | Amsacrine-HCl | Lauryl hydroxyethylimidazoline | −4 | 42 | 46 |

-continued

| Compound 1 | Compound 2 | Compound 3 | Compound 4 | Quarternary TG (% C) | Tertiary (1-3 combo; TG % C) | Difference (<30% = synergy) |
|---|---|---|---|---|---|---|
| Linoleoyl Monoethanolamide (LAMEA) | 1,2-dioctanoyl-sn-glycero-3-phosphoethanol-amide | Amsacrine-HCl | Oleoyl hydroxyethlimidazoline | 5 | 42 | 37 |
| Linoleoyl Monoethanolamide (LAMEA) | 1,2-dioctanoyl-sn-glycero-3-phosphoethanol-amide | Amsacrine-HCl | 7H-Benzimidazol[2,1-a]Benz[de]-isoquinolin-7-one | 8 | 42 | 35 |
| Palmitamide Monoethanolamide | 1,2-dioctanoyl-sn-glycero-3-phosphoethanol-amide | Amsacrine-HCl | Miconazole | 13 | 43 | 30 |
| Palmitamide Monoethanolamide | 1,2-dioctanoyl-sn-glycero-3-phosphoethanol-amide | Amsacrine-HCl | Oleoyl hydroxyethlimidazoline | 3 | 43 | 40 |
| Alpha-Damascone | 1,2-dioctanoyl-sn-glycero-3-phosphoethanol-amide | Amsacrine-HCl | Miconazole | 11 | 48 | 37 |
| Alpha-Damascone | 1,2-dioctanoyl-sn-glycero-3-phosphoethanol-amide | Amsacrine-HCl | Ketoconazole | 13 | 48 | 34 |
| Alpha-Damascone | 1,2-dioctanoyl-sn-glycero-3-phosphoethanol-amide | Amsacrine-HCl | Lauryl hydroxyethylimidazoline | 15 | 48 | 33 |
| Alpha-Damascone | 1,2-dioctanoyl-sn-glycero-3-phosphoethanol-amide | Amsacrire-HCl | Oleoyl hydroxyethlimidazoline | 3 | 48 | 45 |
| Castor oil Methyl Ester Acid (MEA) | Phosphatidyl Choline | Carbenoxolone | 12-Hydroxystearic acid | 3 | 55 | 52 |
| Castor oil Methyl Ester Acid (MEA) | Phosphatidyl Choline | Carbenoxolone | Climbazole | 6 | 55 | 49 |
| Castor oil Methyl Ester Acid (MEA) | Phosphatidyl Choline | Carbenoxolone | Miconazole | −2 | 55 | 57 |
| Castor oil Methyl Ester Acid (MEA) | Phosphatidyl Choline | Carbenoxolone | Ketoconazole | 1 | 55 | 54 |
| Castor oil Methyl Ester Acid (MEA) | Phosphatidyl Choline | Carbenoxolone | Lauryl hydroxyethylimidazoline | 4 | 55 | 51 |
| Castor oil Methyl Ester Acid (MEA) | Phosphatidyl Choline | Carbenoxolone | Oleoyl hydroxyethlimidazoline | 3 | 55 | 52 |
| Castor oil Methyl Ester Acid (MEA) | Phosphatidyl Choline | Carbenoxolone | 7H-Benzimidazo[2,1-a]Benz[de]-isoquinolin-7-one | 11 | 55 | 44 |
| Naringenin | Phosphatidyl Choline | Linoleic Acid | Climbazole | −1 | 45 | 46 |
| Geraniol | Phosphatidyl Choline | Linoleic Acid | Climbazole | 1 | 40 | 39 |
| Acetyl sphingosine (C2 Ceramide) | Phosphatidyl Choline | Linoleic Acid | Climbazole | 0 | 40 | 40 |
| Acetyl sphingosine (C2 Ceramide) | Phosphatidyl Choline | Linolenic Acid | Climbazole | 10 | 40 | 30 |
| Dimethyl imidazolinone | TCC | Amsacrine-HCl | Elaidic acid | 14 | 47 | 33 |
| Dimethyl imidazolinone | TCC | Amsacrine-HCl | Quercetin | 12 | 44 | 32 |
| Dimethyl imidazolincne | TCC | Amsacrine-HCl | Coumarin | 14 | 58 | 44 |
| Hexanoyl sphingosine (C6 Ceramide) | TCC | Glycyrrhetinic Acid | Amino Benzotriazole | 8 | 48 | 40 |
| Alpha-Damascone | TCC | Myristic Acid | Climbazole | 10 | 44 | 34 |

B1/B2/B4/B5 Combination:

| Compound 1 | Compound 2 | Compound 3 | Compound 4 | Quarternary TG (% C) | Tertiary (1-3 combo; TG % C) | Difference (<30% = synergy) |
|---|---|---|---|---|---|---|
| Lyrial | Vanilin | Hexadecanedioic acid | Miconazole | 12 | 48 | 36 |
| Lyrial | Vanilin | Hexadecanedioic acid | Oleoyl hydroxyethlimidazoline | 4 | 48 | 45 |
| Crocetin | TCC | Elaidic acid | 2-Hydroxy-quinoline(Carbostyril) | 11 | 48 | 37 |

-continued

| Compound 1 | Compound 2 | Compound 3 | Compound 4 | Quarternary TG (% C) | Tertiary (1-3 combo; TG % C) | Difference (<30% = synergy) |
|---|---|---|---|---|---|---|
| Hexanoyl sphingosine (C6 Ceramide) | Glycyrrhetinic Acid | 12-Hydroxystearic acid | Amino Benzotriazole | 14 | 48 | 33 |
| Dimethyl imidazolinone | Phosphatidyl Choline | 2-Hydroxystearic acid | 7H-Benzimidazo[2,1-a]Benz[de]-isoquinolin-7-one | 2 | 44 | 42 |
| Melinamide | Phosphatidyl Choline | 2-Hydroxystearic acid | 7H-Benzimidazo[2,1-a]Benz[de]-isoquinolin-7-one | 5 | 44 | 39 |
| Geranyl geraniol | Phosphatidyl Choline | 2-Hydroxystearic acid | 7H-Benzimidazo[2,1-a]Benz[de]-isoquinolin-7-one | 9 | 44 | 35 |
| Cocoyl hydroxyethylimidazoline | Phosphatidyl Choline | 2-Hydroxystearic acid | 7H-Benzimidazo[2,1-a]Benz[de]-isoquinolin-7-one | −8 | 44 | 52 |
| Acetyl sphingosine (C2 Ceramide) | Phosphatidyl Choline | 2-Hydroxystearic acid | 7H-Benzimidazol[2,1-a]Benz[de]-isoquinolin-7-one | 10 | 44 | 34 |
| Crocetin | Phosphatidyl Choline | 2-Hydroxystearic acid | 7H-Benzimidazo[2,1-a]Benz[de]-isoquinolin-7-one | 10 | 44 | 34 |
| N,N-Diethyl Cocamide(Cocamide DEA) | Phosphatidyl Choline | 2-Hydroxystearic acid | 7H-Benzimidazo[2,1-a]Benz[de]-isoquinolin-7-one | 4 | 44 | 40 |
| Cocoyl hydroxyethylimidazoline | Phosphatidyl Choline | Elaidic acid | Climbazole | −4 | 30 | 34 |
| B1/B3/B4/B5 Combination: | | | | | | |
| Dimethyl imidazolinone | Amsacrine-HCl | Elaidic acid | Miconazole | 7 | 47 | 40 |
| Dimethyl imidazolinone | Amsacrine-HCl | Elaidic acid | Ketoconazole | 6 | 47 | 41 |
| Dimethyl imidazolinone | Amsacrine-HCl | Elaidic acid | Oleoyl hydroxyethlimidazoline | 3 | 47 | 44 |
| Hexanoyl sphingosine (C6 Ceramide) | Glycyrrhetinic Acid | Isostearic acid | Clotrimazole | 20 | 54 | 34 |
| Hexanoyl sphingosine (C6 Ceramide) | Glycyrrhetinic Acid | Isostearic acid | Miconazole | 10 | 54 | 43 |
| Hexanoyl sphingosine (C6 Ceramide) | Glycyrrhetinic Acid | Isostearic acid | Lauryl hydroxyethylimidazoline | 20 | 54 | 33 |
| Hexanoyl sphingosine (C6 Ceramide) | Glycyrrhetinic Acid | Isostearic acid | Oleoyl hydroxyethlimidazoline | 5 | 54 | 48 |
| Crocetin | Linoleic Acid | Elaidic acid | 2-Hydroxyquinoline (Carbostyril) | 0 | 48 | 48 |
| Crocetin | Linolenic Acid | Elaidic acid | 2-Hydroxyquinoline (Carbostyril) | −2 | 48 | 50 |
| Castor oil Methyl Ester Acid (MEA) | Linoleic Acid | Elaidic acid | 2-Hydroxyquinoline (Carbostyril) | −1 | 31 | 32 |
| Cocoyl hydroxyethylimidazoline | Carbenoxolone | Elaidic acid | 2-Hydroxyquinoline (Carbostyril) | −6 | 28 | 34 |
| B2/B3/B4/B5 Combination: | | | | | | |
| 1,2-dioctanoyl-sn-glycero-3-phosphoethanol-amide | Glycyrrhetinic Acid | Isostearic acid | Ketoconazole | 4 | 37 | 33 |
| 1,2-dioctanoyl-sn-glycero-3-phosphoethanol-amide | Glycyrrhetinic Acid | Isostearic acid | Oleoyl hydroxyethlimidazoline | 6 | 37 | 31 |
| Phosphatidyl Choline | Arachidonic Acid (Na+ salt) | 2-Hydroxystearic acid | Miconazole | 6 | 37 | 31 |
| Phosphatidyl Choline | Arachidonic Acid (Na+ salt) | 2-Hydroxystearic acid | Oleoyl hydroxyethlimidazoline | 5 | 37 | 32 |
| 1,2-dioctanoyl-sn-glycero-3-phosphoethanolamide | Glycyrrhetinic Acid | Linseed oil | Miconazole | −1 | 45 | 47 |

-continued

| Compound 1 | Compound 2 | Compound 3 | Compound 4 | Quarternary TG (% C) | Tertiary (1-3 combo; TG % C) | Difference (<30% = synergy) |
|---|---|---|---|---|---|---|
| 1,2-dioctanoyl-sn-glycero-3-phosphoethanolamide | Glycyrrhetinic Acid | Linseed oil | Oleoyl hydroxyethlimidazoline | 7 | 45 | 38 |
| Phosphatidyl Choline | Carbenoxolone | 2-Hydroxystearic acid | 7H-Benzimidazo[2,1-a]Benz[de]-isoquinolin-7-one | 8 | 44 | 36 |
| Phosphatidyl Choline | Linoleic Acid | 2-Hydroxystearic acid | 7H-Benzimidazo[2,1-a]Benz[de]-isoquinolin-7-one | −3 | 44 | 47 |
| Phosphatidyl Choline | Glycyrrhetinic Acid | Elaidic acid | Climbazole | −3 | 30 | 33 |
| Phosphatidyl Choline | Linoleic Acid | Elaidic acid | Climbazole | −2 | 30 | 32 |

Cosmetically Acceptable Vehicle

The composition according to the invention also comprises a cosmetically acceptable vehicle to act as a dilutant, dispersant or carrier for the active components in the composition, so as to facilitate their distribution when the composition is applied to the skin.

Vehicles other than or in addition to water can include liquid or solid emollients, solvents, humectants, thickeners and powders. An especially preferred non-aqueous carrier is a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilised in the compositions of this invention range anywhere from 5 to 95%, preferably from 25 to 90% by weight of the composition.

Optional Skin Benefit Materials and Cosmetic Adjuncts

An oil or oily material may be present, together with an emulsifier to provide either a water-in-oil emulsion or an oil-in-water emulsion, depending largely on the average hydrophilic-lipophilic balance (HLB) of the emulsifier employed.

Various types of active ingredients may be present in cosmetic compositions of the present invention. Various types of active ingredients may be present in cosmetic compositions of the present invention. Actives are defined as skin or hair benefit agents other than emollients and other than ingredients that merely improve the physical characteristics of the composition. Although not limited to this category, general examples include sunscreens, skin lightening agents, and tanning agents.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively.

The exact amount of sunscreen employed in the emulsions can vary depending upon the degree of protection desired from the sun's UV radiation.

Another preferred optional ingredient is selected from essential fatty acids (EFAs), i.e., those fatty acids which are essential for the plasma membrane formation of all cells, in keratinocytes EFA deficiency makes cells hyperproliferative. Supplementation of EFA corrects this. EFA's also enhance lipid biosynthesis of epidermis and provide lipids for the barrier formation of the epidermis. The essential fatty acids are preferably chosen from linoleic acid, γ-linolenic acid, homo-γ-linolenic acid, columbinic acid, eicosa-(n-6,9,13)-trienoic acid, arachidonic acid, γ-linolenic acid, timnodonic acid, hexaenoic acid and mixtures thereof.

Emollients are often incorporated into cosmetic compositions of the present invention. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B.F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, Fullers earth, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these materials may range anywhere from 0.001% up to 20% by weight of the composition.

Use of the Composition

The composition according to the invention is intended primarily as a product for topical application to human skin, especially as an agent for conditioning and smoothening the skin, and preventing or reducing the appearance of wrinkled or aged skin.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

Product Form and Packaging

The topical skin treatment composition of the invention can be formulated as a lotion, a fluid cream, a cream or a gel. The composition can be packaged in a suitable container to suit its viscosity and intended use by the consumer. For example, a lotion or fluid cream can be packaged in a bottle or a roll-ball applicator, or a capsule, or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined.

The invention claimed is:

1. A method for treating skin comprising the steps of:
   (i) applying to the skin a composition comprising:
      (a) from 0.01% to 10% of a retinoid;
      (b) at least one booster compound selected from the group consisting of farnesol, glycyrrhetinic acid and ursolic acid;
      (c) a cosmetically acceptable vehicle, and
   (ii) treating the skin for wrinkles, psoriasis, age spots and/or discoloration.

2. The method according to claim 1 wherein the composition further comprises an additional compound which is climbazole, linoleic acid, myristic acid, 12-hydroxystearic acid or a mixture thereof.

3. The method according to claim 2 wherein the composition further comprises climbazole.

4. The method according to claim 1 wherein the skin care composition further comprises a fatty alcohol or fatty acid.

5. The method according to claim 1 where the booster compound or compounds make up from about 0.0001% to 50% of the composition.

6. The method according to claim 1 wherein the booster compound or compounds potentiate the action of retinoids by increasing conversion of retinoid to retinoic acid and further wherein the compound or compounds cause an action which is an inhibition of ARAT/LRAT activity, an enhancement of retinol dehydrogenase activity, an inhibition of retinal reductase activity, antagonistic to CRABP-II binding of retinoic acid and/or an inhibition of cytochrome P450 dependent retinoic acid oxidation.

7. The method according to claim 4 wherein the composition further comprises climbazole and the fatty alcohol is cetyl alcohol.

8. The method according to claim 4 wherein the composition further comprises bifonazole and the fatty alcohol is cetyl alcohol.

9. The method according to claim 1 wherein the composition comprises glycyrrhetinic acid.

10. The method according to claim 1 wherein the composition comprises farnesol.

11. The method according to claim 1 wherein the composition comprises ursolic acid.

12. The method according to claim 1 wherein the composition further comprises a sunscreen.

13. The method according to claim 1 wherein the composition further comprises linoleoyl monoethanolamide, palmitamide monoethanolamide, castor oil methyl ester acid, skin lightening agent or a mixture thereof.

14. The method according to claim 1 wherein the composition further comprises 12-hydroxystearic acid.

* * * * *